(12) United States Patent
Lee et al.

(10) Patent No.: US 7,538,239 B2
(45) Date of Patent: May 26, 2009

(54) TRANSITION METAL COMPLEXES, CATALYST COMPOSITIONS CONTAINING THE SAME, AND OLEFIN POLYMERIZATION USING THE CATALYST COMPOSITIONS

(75) Inventors: Choong Hoon Lee, Daejeon (KR); Eun Jung Lee, Daejeon (KR); Seungwhan Jung, Suwon (KR); Jong Joo Ha, Daejeon (KR); Beomdoo Seo, Daejeon (KR); Bun Yeoul Lee, Suwon (KR); Ui Gab Joung, Suwon (KR); Dae June Joe, Bucheon (KR)

(73) Assignee: LG Chem, Ltd. (KR)

( * ) Notice: Subject to any disclaimer, the term of this patent is extended or adjusted under 35 U.S.C. 154(b) by 186 days.

(21) Appl. No.: 11/483,514

(22) Filed: Jul. 10, 2006

(65) Prior Publication Data
US 2007/0010637 A1    Jan. 11, 2007

(30) Foreign Application Priority Data
Jul. 8, 2005    (KR) .................... 10-2005-0061820

(51) Int. Cl.
  *C07F 7/00*    (2006.01)
  *C08F 7/28*    (2006.01)
(52) U.S. Cl. ..................... 556/52; 556/51; 526/161; 526/172
(58) Field of Classification Search .............. 556/52; 526/172
  See application file for complete search history.

(56) References Cited

U.S. PATENT DOCUMENTS

| | | | |
|---|---|---|---|
| 5,064,802 A | 11/1991 | Stevens et al. | 502/155 |
| 5,856,258 A | 1/1999 | Marks et al. | |
| 6,090,739 A * | 7/2000 | Riedel et al. | 502/103 |
| 6,548,686 B2 * | 4/2003 | Nabika et al. | 556/51 |
| 2004/0242410 A1 * | 12/2004 | Hanaoka et al. | 502/117 |

FOREIGN PATENT DOCUMENTS

JP    2001158753    6/2001

(Continued)

OTHER PUBLICATIONS

Chen, Y., "A Novel Phenolate "Constrained Geometry" Catalyst System. Efficient Synthesis, Structural Characterization, and a-Olefin Polymerization Catalysis," Organometallics, vol. 16, pp. 5958-5963 (1997).

(Continued)

*Primary Examiner*—Vasu Jagannathan
*Assistant Examiner*—Rip A. Lee
(74) *Attorney, Agent, or Firm*—Cantor Colburn LLP

(57) ABSTRACT

Provided are a novel transition metal complex where a mono-cyclopentadienyl ligand to which an amido or alcoxy group is introduced is coordinated, a method of synthesizing the same, and olefin polymerization using the transition metal complex. Compared to a conventional transition metal complex having a silicon bridge and an oxido ligand, the transition metal complex has a phenylene bridge, so that a monomer easily approaches the transition metal complex in terms of structure and a pentagon ring structure of the transition metal complex is stably maintained. The catalyst composition including the transition metal complex is used to synthesize a polyolefin copolymer having a very low density less than 0.910 g/cc.

8 Claims, 3 Drawing Sheets

FOREIGN PATENT DOCUMENTS

| JP | 2003-221396 | * | 8/2003 |
| KR | 1020050028664 | | 3/2005 |
| WO | 9912940 | | 3/1999 |
| WO | 03024983 | | 3/2003 |

OTHER PUBLICATIONS

Gielens, E., "Titanium Hydrocarbyl Complexes with a Linked Cyclopentadienyl-Alkoxide Ancillary Ligand; Participation of the Ligand in an Unusual Activation of a (Trimethylsilyl)methyl Group," Organometallics, vol. 17, pp. 1652-1654 (1998).

Christie, S., et al., "Novel Routes to Bidentate Cyclopentadienyl-Alkoxide Complexes of Titanium: Synthesis of (n5-o-C5R14CHR2CR3R4O) TiCl2," Organometallics, vol. 18, pp. 348-359 (1999).

Rau, A., et al., "Synthesis and Application in High-Pressure Polymerization of a Titanium Complex with a Linked cyclopentadienyl-phenoxide Ligand," Journal of Organometallic Chemistry, vol. 608, pp. 71-75 (2000).

Turner, L., et al., "Facile Resolution of Constrained Geometry Indenyl-phenoxide Ligation," ChemComm, pp. 1034-1035 (2003).

Gibson, V., et al., "Advances in Non-Metallocene Olefin Polymerization Catalysis" Chem. Rev., vol. 103, pp. 283-315 (2003).

Zhang, Y., et al., "Tetramethylcyclopentadienyl-phenoxytitanium Dichlorides: Template Synthesis, Structures, and Catalytic Properties for Ethylene Polymerization," Organometallics, vol. 23, pp. 540-546 (2004).

Korean Office Action dated May 29, 2007 for Application No. 10-2005-0061820 (All references cited in the Office Action are listed above).

* cited by examiner

TRANSITION METAL COMPLEXES, CATALYST COMPOSITIONS CONTAINING THE SAME, AND OLEFIN POLYMERIZATION USING THE CATALYST COMPOSITIONS

CROSS-REFERENCE TO RELATED PATENT APPLICATIONS

This application claims the benefit of Korean Patent Application No. 10-2005-0061820, filed on Jul. 8, 2005, in the Korean Intellectual Property Office, the disclosure of which is incorporated herein in its entirety by reference.

BACKGROUND OF THE INVENTION

1. Field of the Invention

The present invention relates to a novel transition metal complex where a monocyclopentadienyl ligand to which an amido or alcoxy group is introduced is coordinated, a method of synthesizing the same, and olefin polymerization using the transition metal complex, and more particularly, to a novel transition metal complex containing a phenylene bridge, a method of synthesizing the same, and olefin polymerization using the transition metal complex.

2. Description of the Related Art

In the early 1990s, Dow Co. developed Me$_2$Si(Me$_4$C5)(NtBu)TiCl$_2$ (Constrained-Geometry Catalyst, hereinafter referred to as CGC) (U.S. Pat. No. 5,064,802). CGC shows excellent properties in a copolymerization reaction of ethylene and alpha-olefin, compared to conventional metallocene catalysts. For example, (1) CGC can be used to form high molecular weight polymers due to its high reactivity at high polymerization temperature, and (2) CGC can be used for copolymerization of alpha-olefin having large steric hindrance, such as 1-hexene and 1-octene. Due to many useful properties, in addition to these properties described above, obtained from use of CGC, research into synthesis of CGC derivatives as a polymerization catalyst is substantially increasing in academic and industrial fields.

For example, synthesis of metal complexes comprising other various bridges instead of a silicon bridged CGC and containing a nitrogen substituent, and polymerization using these metal complexes were performed. Examples of such metal compounds include Complexes 1 through 4 (*Chem. Rev.* 2003, 103, 283).

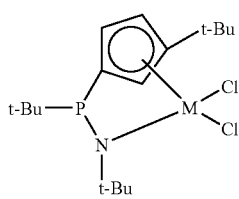

(1)

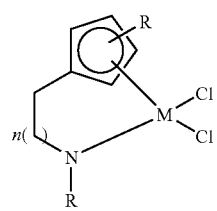

(2)

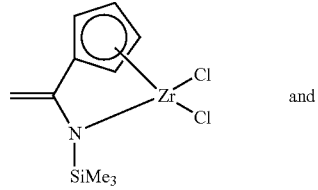

(3)

and

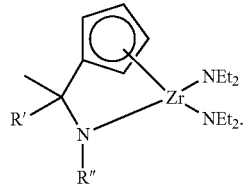

(4)

Complexes 1 through 4 respectively contain a phosphorus bridge, an ethylene or propylene bridge, a methylidene bridge, and a methylene bridge, instead of the silicon bridge of the CGC structure. However, these complexes show low activity or poor copolymerization performance when ethylene is polymerized or when ethylene and alpha-olefin are copolymerized, compared to CGC.

In addition, the amino ligand in CGC can be replaced with an oxido ligand. some of such complexes were used for polymerization. Examples of such complexes include:

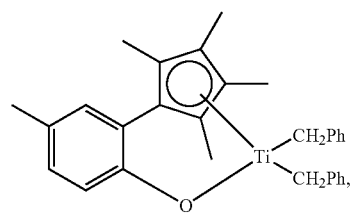

(5)

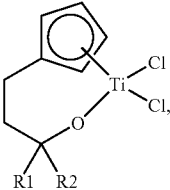

(6)

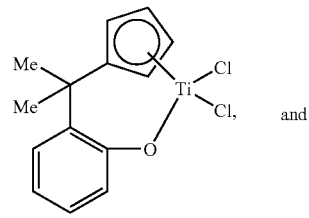

(7)

and

In Complex 5, which was developed by T. J. Marks et al., a cyclopentadiene (Cp) derivative is bridged to an oxido ligand by ortho-penylene group (*Organometallics* 1997, 16, 5958). A complex having the same bridge and polymerization using the compound were suggested by Mu et al. (*Organometallics* 2004, 23, 540). A complex in which an indenyl ligand is bridged to an oxido ligand by an ortho-phenylene group was developed by Rothwell et al. (*Chem. Commun.* 2003, 1034). In Complex 6, which was developed by Whitby et al., a cyclopentadienyl ligand is bridged to an oxido ligand by three carbon atoms (*Organometallics* 1999, 18, 348). It was reported that Complex 6 showed reactivity in syndiotactic polystyrene polymerization. Similar complexes to Complex 6 were developed by Hessen et al. (*Organometallics* 1998, 17, 1652). Complex 7, which was developed by Rau et al., showed reactivity when being used for ethylene polymerization and ethylene/1-hexen copolymerization at high temperature and high pressure (210° C., 150 Mpa) (*J. Organomet. Chem.* 2000, 608, 71). Complex 8, which has a similar structure to Complex 7, can be used for high temperature, high pressure polymerization, which was applied to US Patent Office by Sumitomo Co. (U.S. Pat. No. 6,548,686).

However, only some of these catalysts described above are used in commercial industry. Accordingly, there is still a need to develop a catalyst inducing high polymerization performance.

SUMMARY OF THE INVENTION

The present invention provides a novel transition metal complex having a phenylene bridge.

The present invention also provides a novel organic amine-based compound.

The present invention also provides a novel organic ketone-based boronic acid compound.

The present invention also provides a method of preparing the transition metal complex.

The present invention also provides a catalyst composition containing the transition metal complex.

The present invention also provides a method of preparing the catalyst composition.

The present invention also provides a method of preparing a polymer using the catalyst composition.

The present invention also provides a polymer prepared using the method of preparing a polymer using the catalyst composition.

According to an aspect of the present invention, there is provided a transition metal complex of Formula 1:

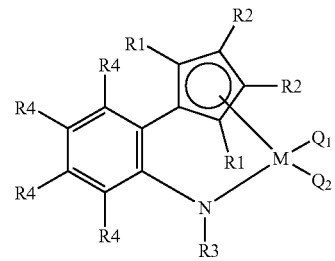

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring;

$R_4$ is each independently a hydrogen atom; a halogen radical; or a C1-C20 alkyl or aryl radical, wherein two $R_4$ are connected to form a fused ring structure;

$R_3$ is a C1-C20 alkyl sulfonyl, aryl sulfonyl, or silyl sulfonyl radical; a C1-C20 alkyl carbonyl, aryl carbonyl, or silyl carbonyl radical; C1-C20 alkyl carboxy, or aryl carboxy radical; or C1-C20 alkyl phosphonyl, or aryl phosphonyl radical;

M is a transition metal of Group 4; and $Q_1$ and $Q_2$ are each independently a halogen radical; a C1-C20 alkyl or aryl amido radical; a C1-C20 alkyl, alkenyl, aryl, alkylaryl, or arylalkyl radical; or a C1-C20 alkylidene radical.

The transition metal complex of Formula 1 may be represented by Formula 14:

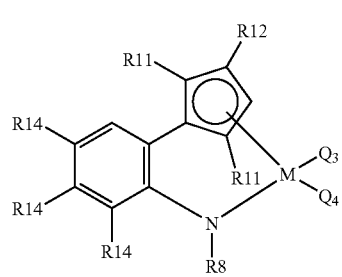

where $R_{11}$ and $R_{12}$ are each independently hydrogen atom; or C1-C20 alkyl, aryl, or silyl radical;

$R_{14}$ is each independently hydrogen atom; a C1-C20 alkyl radical; or halogen radical;

$Q_3$ and $Q_4$ are each independently a halogen radical; C1-C20 alkyl, or aryl amido radical; or C1-C20 alkyl radical;

M is a transition metal of Group 4; and $R_8$ is

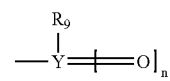

where Y is a carbon atom or a sulfur atom;

$R_9$ is a hydrogen atom; a C1-C20 alkyl, aryl, or silyl radical; or a C1-C20 alkoxy, or aryloxy radical; and when Y is the carbon atom, n is 1, and when Y is the sulfur atom, n is 2.
The transition metal complex of formula 1 may be represented by one of formulae below:
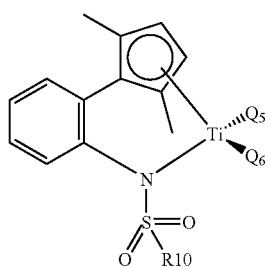
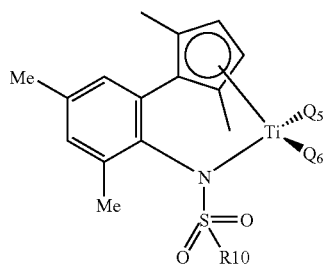
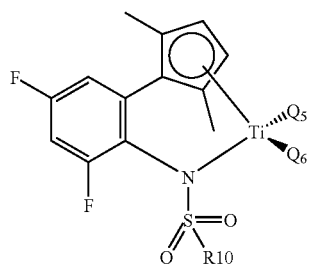
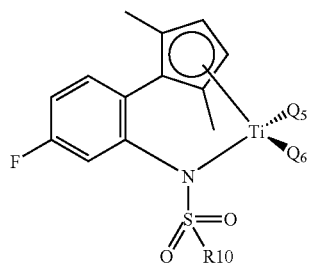
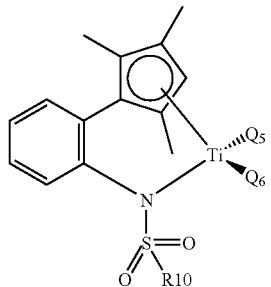
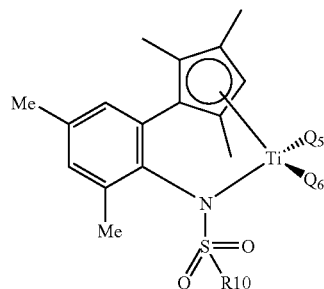
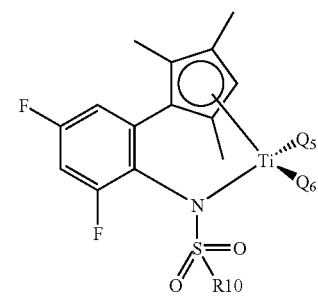
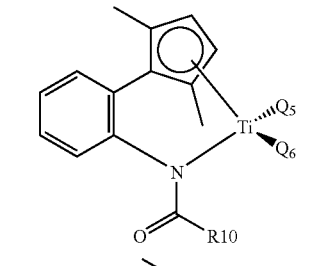
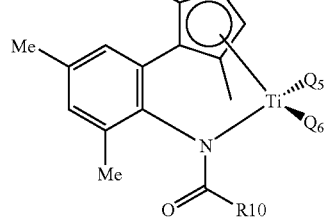
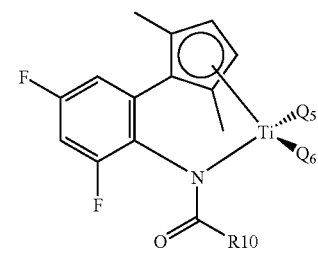
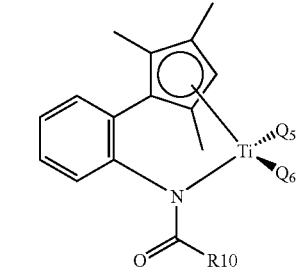

-continued

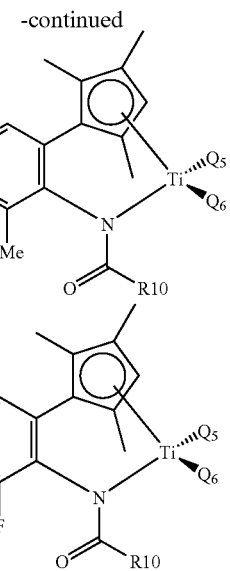

where $R_{10}$ is methyl, tosyl, mesityl, or t-butyl radical; $Q_5$ and $Q_6$ are each independently methyl a dimethylamido radical or a chloride radical.

According to another aspect of the present invention, there is provided a transition metal complex of Formula 2:

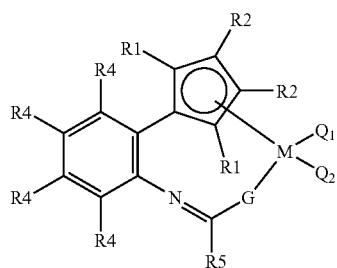

(2)

where $R_1$, $R_2$, $R_4$, M, $Q_1$ and $Q_2$ are described above;
G is an oxygen atom or a sulfur atom; and
$R_5$ is a hydrogen atom; a C1-C20 alkyl or aryl radical; or a C1-C20 alcoxy or aryloxy radical.

According to another aspect of the present invention, there is provided a transition metal complex of Formula 3:

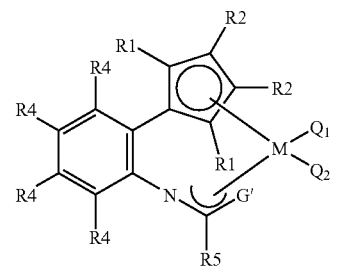

(3)

where $R_1$, $R_2$, $R_4$, $R_5$, M, $Q_1$, and $Q_2$ are described above; and G' is an oxygen atom, a sulfur atom, or a substituted nitrogen group (—NR) where R is a C1-C20 alkyl or aryl radical.

The transition metal complexes of formula 2 or formula 3 may be represented by:

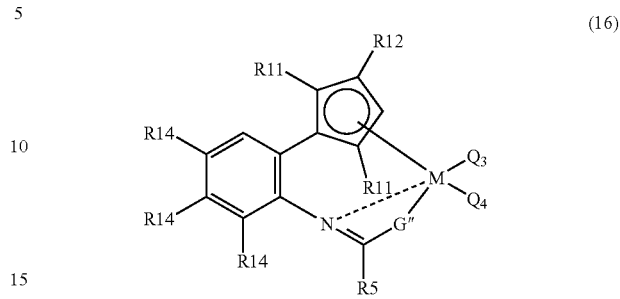

(16)

where $R_{11}$, $R_{12}$, $R_{14}$, $Q_3$, $Q_4$, M, and $R_5$ are described above, and G" is an oxygen atom, a sulfur atom, or a substituted nitrogen group where a substituent is a C1-C20 alkyl or aryl amido radical.

The transition metal complexes of formula 2 or formula 3 may be represented by one of formulae below:

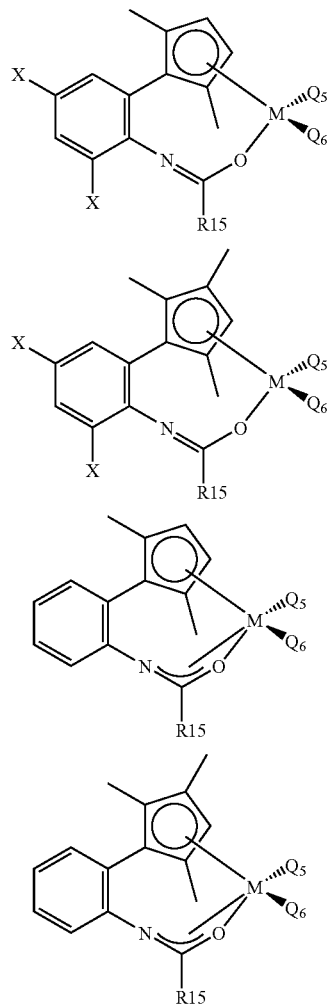

-continued

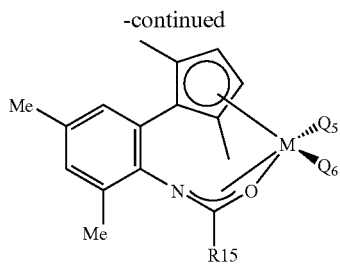

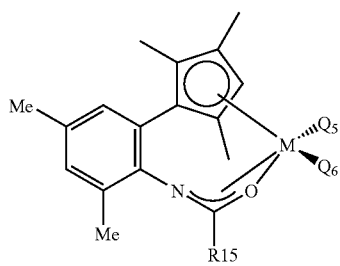

where $R_{15}$ is methyl radical, t-butyl radical, or t-butoxy radical; $Q_5$ and $Q_6$ are described above; and X is a halogen radical.

According to another aspect of the present invention, there is provided amine-based compounds of Formulae 4 through Formula 7:

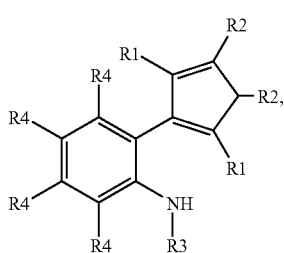 (4)

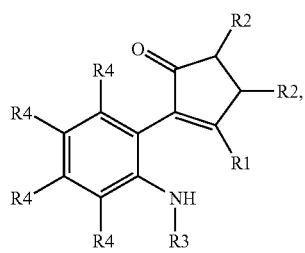 (5)

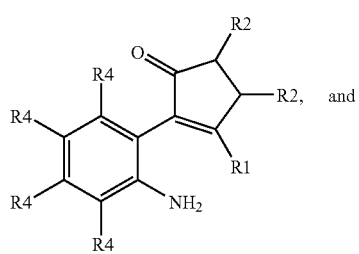 (6)

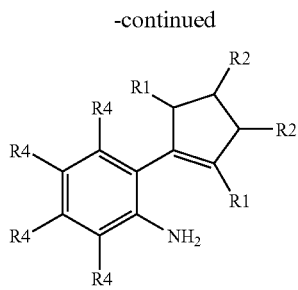 (7)

where $R_1$, $R_2$, $R_3$, and $R_4$ are described above.

According to another aspect of the present invention, there is provided an organic ketone-based boronic acid compound of Formula 8:

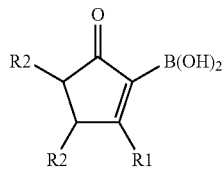 (8)

where $R_1$ and $R_2$ are described above.

According to another aspect of the present invention, there is provided a method of synthesizing a transition metal complex, the method including:

synthesizing a compound of Formula 6 by reacting a boronic acid compound of Formula 8 with a 2-bromoaniline compound of Formula 9;

synthesizing a compound of Formula 5 by the compound of Formula 6 with $R_3X$ where X is a halogen atom;

synthesizing a compound of Formula 4 by reacting a compound of Formula 5 with $R_1Li$ and then adding an acid thereto; and synthesizing a complex of Formula 1 or Formula 2 by reacting the compound of Formula 4 with the compound of Formula 10 and then adding $(CH_3)_nSiX_{4-n}$ where X is a halogen atom and n is 0, 1, 2, or 3 thereto:

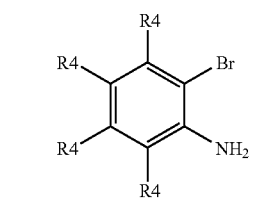 (9)

where $R_4$ is each independently a hydrogen atom; a halogen radical; or a C1-C20 alkyl or aryl radical, wherein two $R_4$ are connected to form a fused ring structure; and $$M(N(R_6)_2)_4 \quad (10)$$

where M is a transition metal of Group 4, and
$R_6$ is a C1-C20 alkyl or aryl radical.

According to another aspect of the present invention, there is provided a method of synthesizing a transition metal complex, the method including:

synthesizing a compound of Formula 6 by reacting a boronic acid compound of Formula 8 with a 2-bromoaniline compound of Formula 9;

synthesizing a compound of Formula 7 by the compound of Formula 6 with $R_1Li$ and then adding an acid thereto;

synthesizing a compound of Formula 4 by reacting a compound of Formula 7 with $R_3X$ where X is a halogen atom; and synthesizing a complex of Formula 1 or Formula 2 by reacting the compound of Formula 4 with the compound of Formula 10 and then adding $(CH_3)_n SiX_{4-n}$ where X is a halogen atom and n is 0, 1, 2, or 3 thereto.

According to another aspect of the present invention, there is provided a method of synthesizing a transition metal complex, the method comprising:

synthesizing a dilithium form of the compound of Formula 7 by reacting a compound of Formula 7 with an alkyllithium that is a base; and synthesizing a complex of Formula 3 by reacting an in-situ mixture composed of the dilithium compound, alkyllithium, and $MX_4$ where X is halogen and M is a transition metal of Group 4.

According to another aspect of the present invention, there is provided catalyst composition including:

the transition metal complex of any one of formulaes 1, 2, and 3; and at least one cocatalyst compound selected from compounds of Formulae 11 through 13:

—[Al(R_7)—O]_a—     (11)

where $R_7$ is each independently a halogen radical; a C1-C20 hydrocarbyl radical; or a C1-C20 hydrocarbyl radical substituted with halogen; and a is an integer of 2 or greater;

D(R_7)_3     (12)

where D is aluminum or boron; and $R_7$ is described above; and

[L—H]⁺[Z(A)_4]⁻, or [L]⁺[Z(A)_4]⁻     (13)

where L is a neutral or cationic Lewis acid;

H is a hydrogen atom;

Z is an element of Group 13;

A is each independently a C6-C20 aryl or alkyl radical in which at least one hydrogen atom is substituted with halogen or a C1-C20 hydrocarbyl, alcoxy, or phenoxy radical.

According to another aspect of the present invention, there is provided a method of preparing a catalyst composition, the method including:

contacting the transition metal complex of any one of formulaes 1, 2, and 3 with the compound of Formula 11 or Formula 12, thereby obtaining a mixture; and adding a compound of Formula 13 to the mixture.

The mole ratio of the transition metal complex to the compound of Formula 11 or Formula 12 may be in the range of 1:2 through 1:5000, and the mole ratio of the transition metal complex of the compound of Formula 13 may be in the range of 1:1 through 1:25.

According to another aspect of the present invention, there is provided a method of synthesizing an olefin polymer, including contacting the catalyst composition with a monomer.

The monomer may contain at least one monomer selected from the group consisting of ethylene, propylene, 1-butene, 1-pentene, 4-methyl-1-pentene, 1-hexene, 1-hepthene, 1-octene, 1-decene, 1-undecene, 1-dodecene, 1-tetradecene, 1-hexadecene, and 1-itosen.

According to another aspect of the present invention, there is provided an olefin polymer synthesized using the method of synthesizing an olefin polymer.

The monomer that is used to synthesize the olefin polymer may include: ethylene; and at least one compound selected from the group consisting of propylene, 1-butene, 1-hexene, 4-methyl-1-pentene, and 1-octene.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings.

A transition metal complex according to an embodiment of the present invention has a phenylene bridge, so that a sterically hindered monomer easily approaches the transition metal complex and a pentagon ring structure of the transition metal complex is stably maintained, compared to a conventional transition metal complex having a silicon bridge and an oxido ligand. By using a catalyst composition including the transition metal complex according to an embodiment of the present invention, a polyolefin copolymer having a very low density less than 0.910 g/cc can be obtained.

A transition metal complex according to an embodiment of the present invention may be represented by Formula 1:

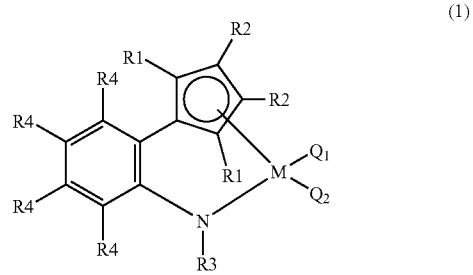

(1)

where $R_1$ and $R_2$ are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein $R_1$ and $R_2$ can be connected by an alkylidine radical that contains a C1-C20 alkyl or aryl radical to form a ring; $R_4$ is each independently a hydrogen atom; a halogen radical; or a C1-C20 alkyl or aryl radical, wherein two $R_4$ can be connected to form a fused ring structure; $R_3$ is a C1-C20 alkyl sulfonyl, aryl sulfonyl, or silyl sulfonyl radical; a C1-C20 alkyl carbonyl, aryl carbonyl, or silyl carbonyl radical; C1-C20 alkyl carboxy, or aryl carboxy radical; or C1-C20 alkyl phosphonyl, or aryl phosphonyl radical; M is a transition metal of Group 4; and $Q_1$ and $Q_2$ are each independently a halogen radical; a C1-C20 alkyl or aryl amido radical; a C1-C20 alkyl, alkenyl, aryl, alkylaryl, or arylalkyl radical; or a C1-C20 alkylidene radical.

Figure 1:
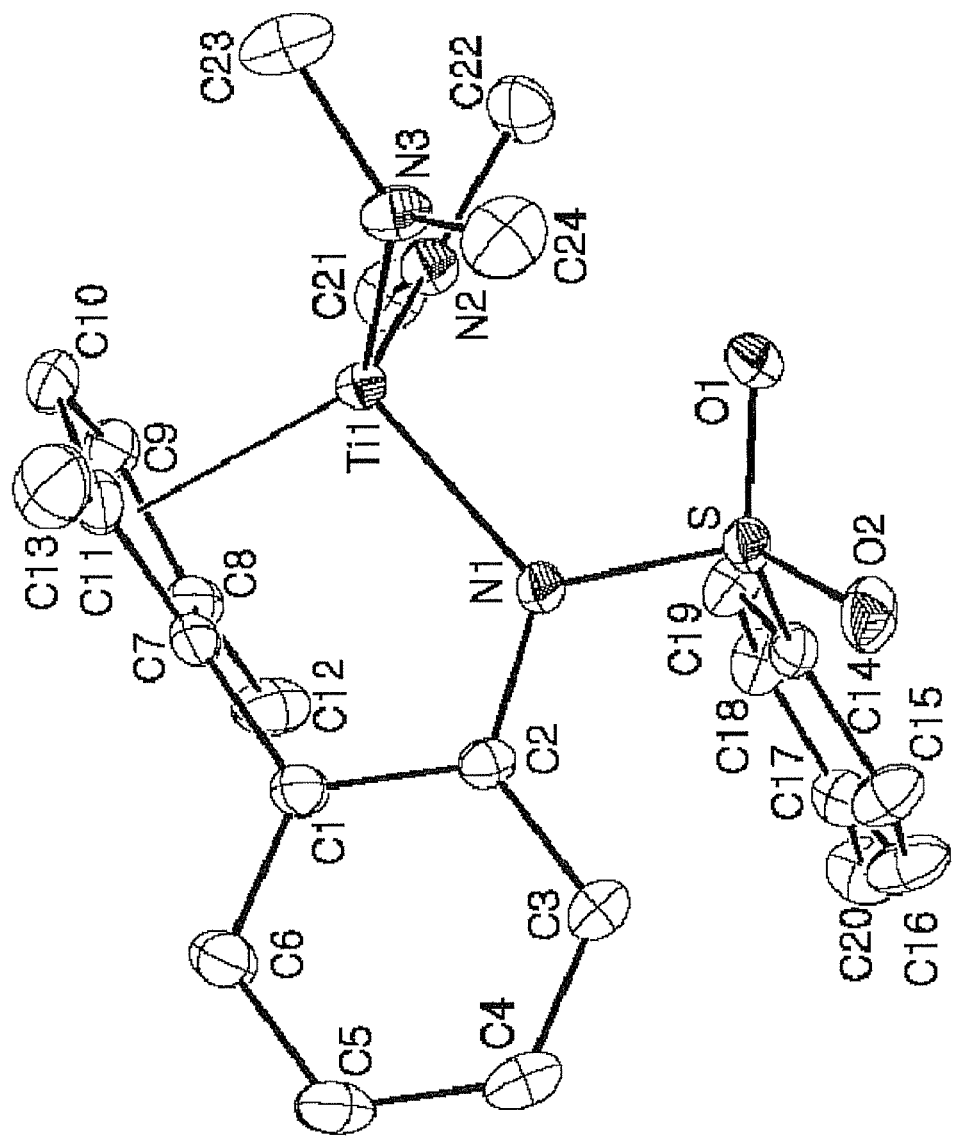
FIG. 1 illustrates an X-ray structure of (p-toluenesulfonylamido)(2,5-dimethylcyclopentadienyl)titanium bis(dimethylamide) that is a transition metal complex according to an embodiment of the present invention.

In the transition metal complex of Formula 1 according to an embodiment of the present invention, a cyclopentadienyl derivative is connected to an amido group by a phenylene bridge such that a Cp—M—N angle is small but a $Q_1$—M—$Q_2$ angle to which a monomer approaches is large, which is illustrated in FIG. 1. In addition, compared to a CGC structure that includes a silicon bridge, the complex of Formula 1 has a stable, strong pentagon ring where Cp, a phenylene bridge, and nitrogen are connected to a metal site. Accordingly, when the complex of Formula 1 which is activated by a cocatalyst, such as methylaluminoxane, or B(C6F$_5$)$_3$, is applied to the synthesis of polyolefin, a polyolefin with high molecular weight, and high degree of copolymerization an be obtained even at high reaction temperature. Due to such structural feature of the complex of Formula 1, a linear low density polyethylene having a density of 0.910-0.930 g/cc. In addition, since a great amount of alpha-olefin can be comprised, a polyolefin copolymer having a very low density less than 0.910 g/cc can be obtained. In addition, various substituents can be introduced to a cyclopentadienyl ring, nitrogen, and a phenylene ring so that electronic and steric environments in the vicinity of metal can be easily controlled to obtain desired structure and properties of a polymer which will be formed. The transition metal complex according to an embodiment of the present invention is used to prepare a catalyst that is used to polymerize olefin monomers. However, use of the transition metal complex is not limited thereto, that is, the transition metal complex can be used in any application to which the transition metal complex can be used.

The compound of Formula 1 may have the structure corresponding to Formula 14, which is preferred to control electronic, steric environments in the vicinity of metal:

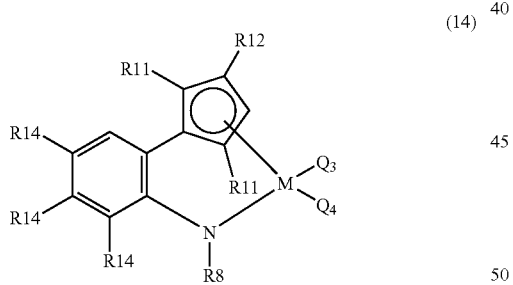

(14)

where $R_{11}$ and $R_{12}$ are each independently hydrogen atom; or C1-C20 alkyl, aryl, or silyl radical;

$R_{14}$ is each independently hydrogen atom; a C1-C20 alkyl radical; or halogen radical;

$Q_3$ and $Q_4$ are each independently a halogen radical; C1-C20 alkyl, or aryl amido radical; or C1-C20 alkyl radical;

M is a transition metal of Group 4; and $R_8$ is

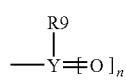

where Y is a carbon atom or a sulfur atom;

$R_9$ is a hydrogen atom; a C1-C20 alkyl, aryl, or silyl radical; or a C1-C20 alcoxy, or aryloxy radical; and when Y is the carbon atom, n is 1, and when Y is the sulfur atom, n is 2.

The transition metal complex of Formula 1 may be a compound of one of the formulae below:

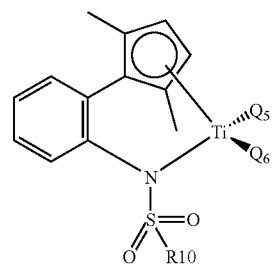

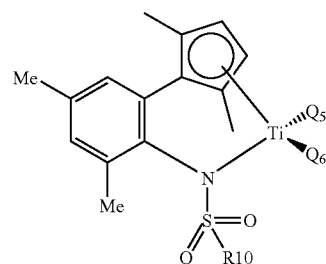

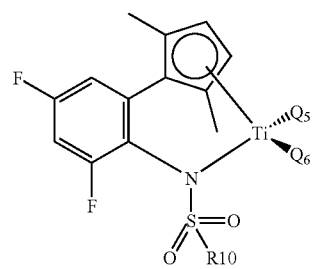

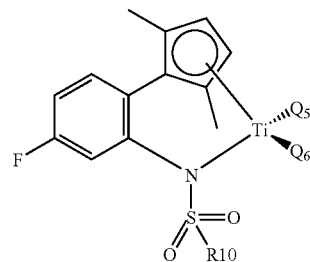

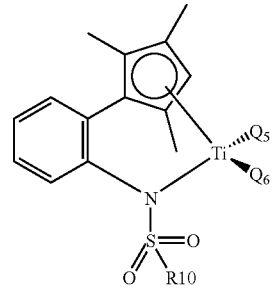

-continued

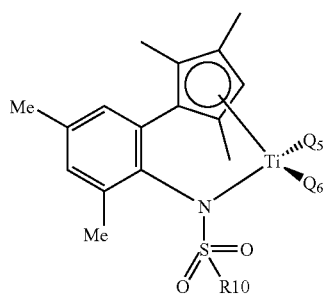

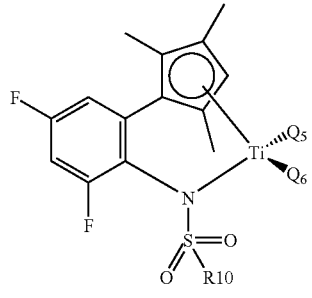

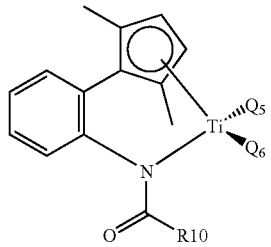

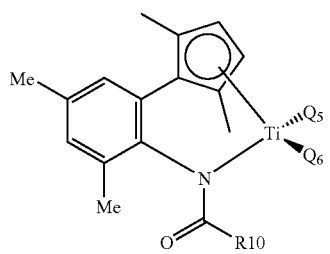

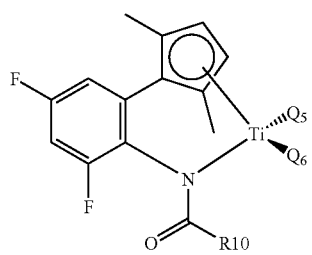

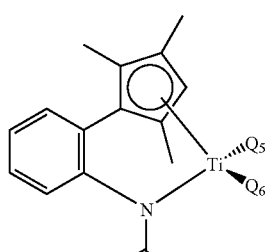

-continued

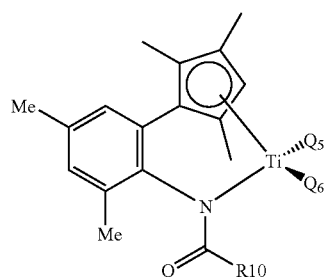

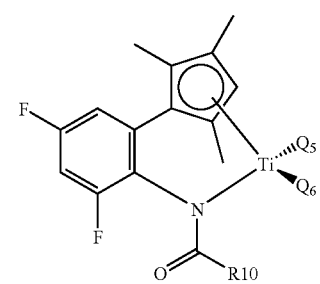

where $R_{10}$ is a methyl radical, a tosyl radical, a mesityl radical, or t-butyl radical; $Q_5$ and $Q_6$ are each independently a methyl radical, a dimethylamido radical, or a chloride radical.

Figure 2:
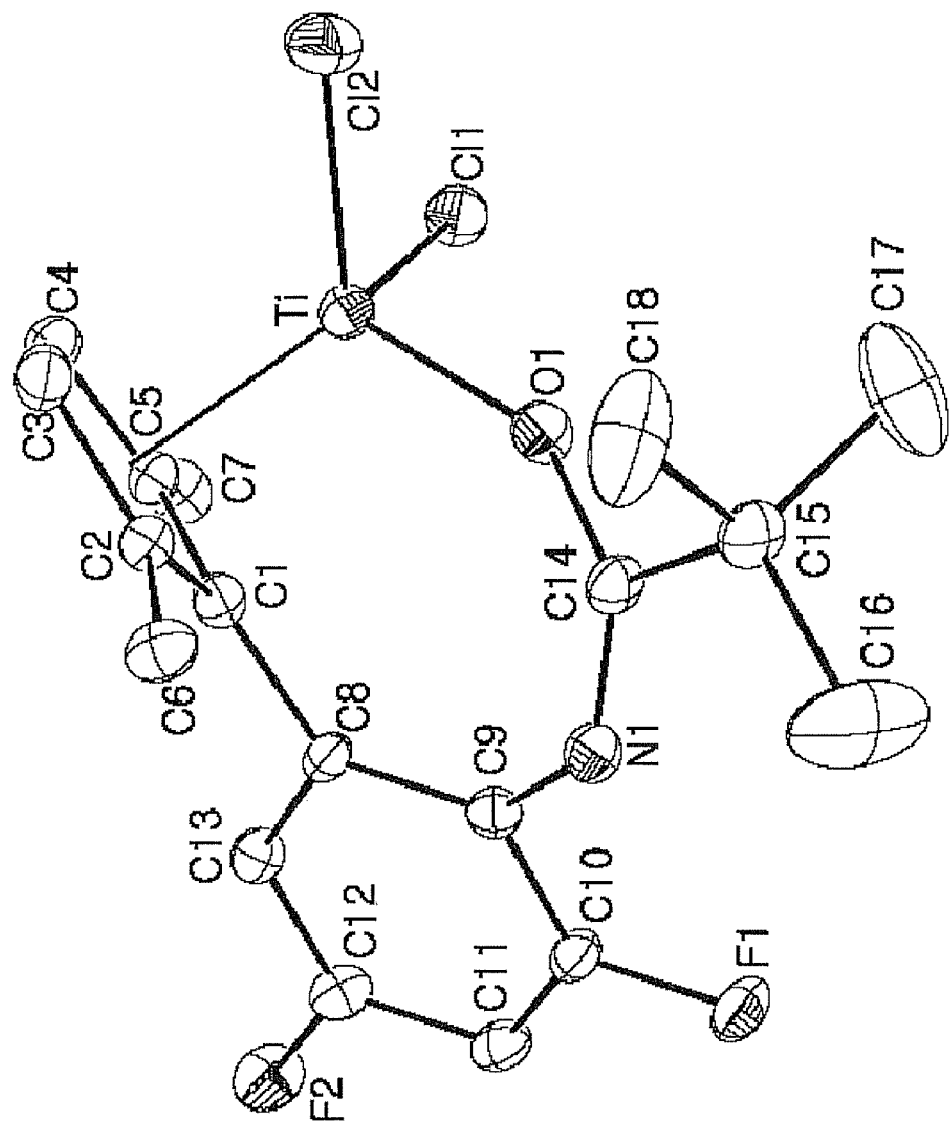
FIG. 2 illustrates an X-ray structure of 4,6-difluorophenylene(t-butyliminooxy)(2,5-dimethylcyclopentadienyl)-titanium dichloride that is a transition metal complex according to another embodiment of the present invention.
Figure 3:
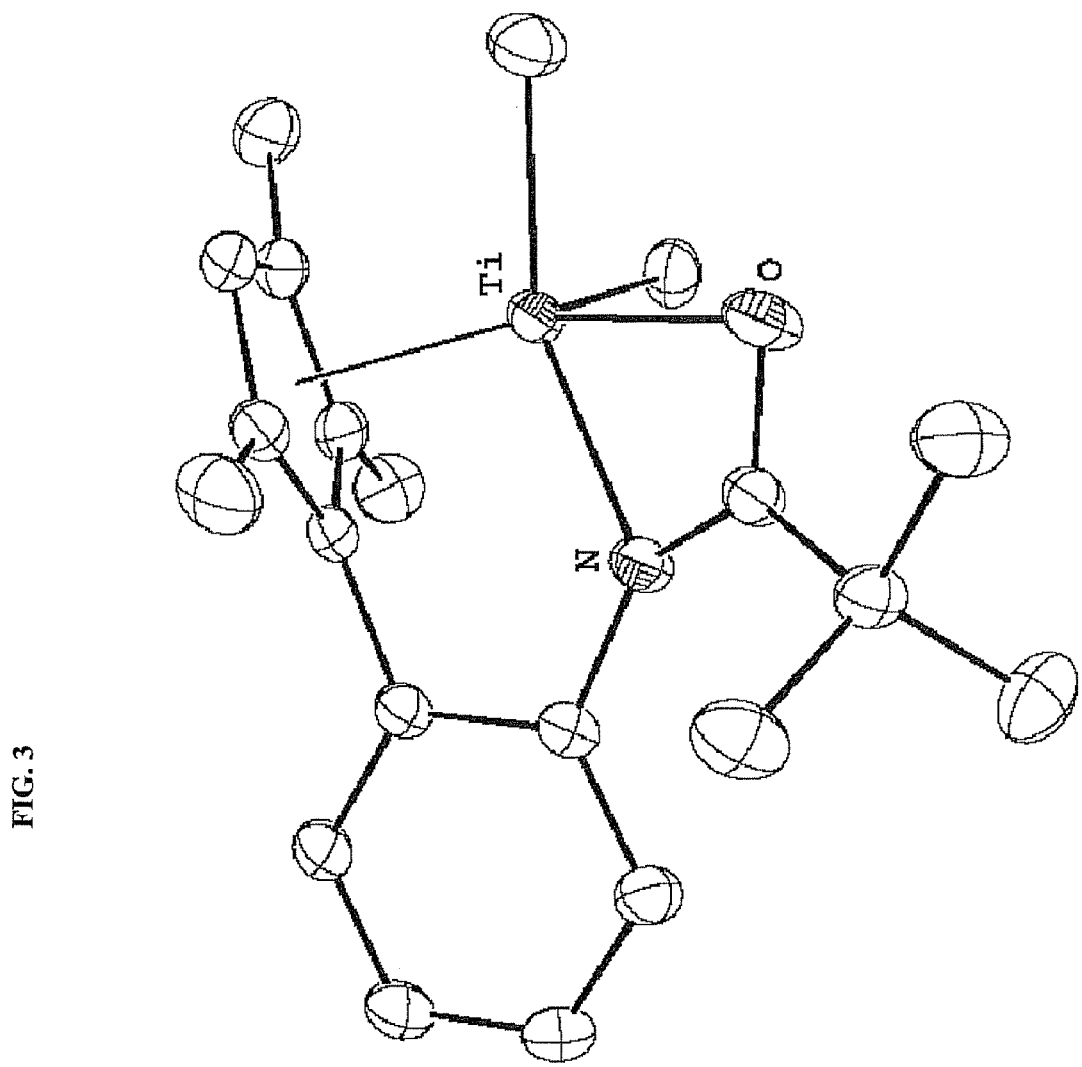
FIG. 3 illustrates an X-ray structure of phenylene(t-butylcarboxamido)(2,5-dimethylcyclopentadienyl)titanium dimethyl that is a transition metal complex according to another embodiment of the present invention.

Transition metal complexes according to another embodiment of the present invention are represented by Formulae 2 and 3 where N or G, which is a heteroatom, are bound to metal. These transition metal complexes may have a chemical structure of $\eta^1$-G bonding mode (Formula 2) or $\eta^2$-N,G bonding mode (Formula 3), according to a substituent of a cyclopentadienyl ring or phenylene bridge, or a method of synthesizing a complex. Structures of these complexes are illustrated in FIGS. 2 and 3:

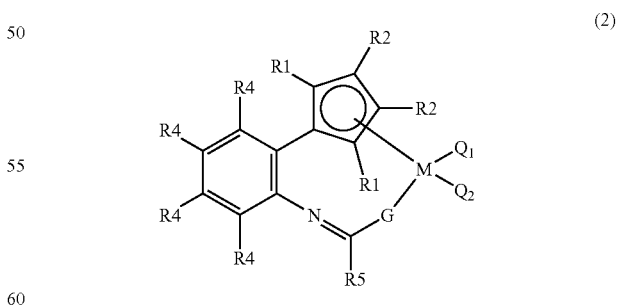

(2)

where $R_1$, $R_2$, $R_4$, M, $Q_1$ and $Q_2$ are described above; G is an oxygen atom or a sulfur atom; and $R_5$ is a hydrogen atom; a C1-C20 alkyl or aryl radical; or a C1-C20 alcoxy or aryloxy radical.

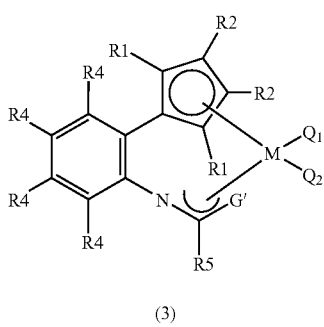

<Formula 3>

(3)

where $R_1$, $R_2$, $R_4$, $R_5$, M, $Q_1$, and $Q_2$ are described above; and G' is an oxygen atom, a sulfur atom, or a substituted nitrogen group (—NR) where R is a C1-C20 alkyl or aryl radical. These transition metal complexes according to another embodiment of the present invention are used to prepare a catalyst that is used to polymerize olefin monomers. However, use of these transition metal complexes is not limited thereto, that is, the transition metal complexes can be used in any application to which the transition metal complex can be used.

The transition metal complex of Formula 2 or Formula 3 may have the structure corresponding to Formula 16, which is preferred to control electronic, steric environments in the vicinity of metal:

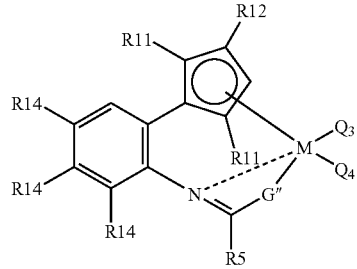

(16)

where $R_{11}$ and $R_{12}$ are each independently hydrogen atom; or C1-C20 alkyl, aryl, or silyl radical;

$R_{14}$ is each independently a hydrogen atom; a C1-C20 alkyl radical; or a halogen radical;

$Q_3$ and $Q_4$ are each independently a halogen radical; a C1-C20 alkyl or aryl amido radical; or a C1-C20 alkyl radical;

M and $R_5$ are described above; and

G" is a oxygen atom, a sulfur atom, or a substituted nitrogen group where a substituent is a C1-C20 alkyl or aryl amido radical.

The transition metal complex of Formula 2 or Formula 3 may be a compound of any one of the formulae below:

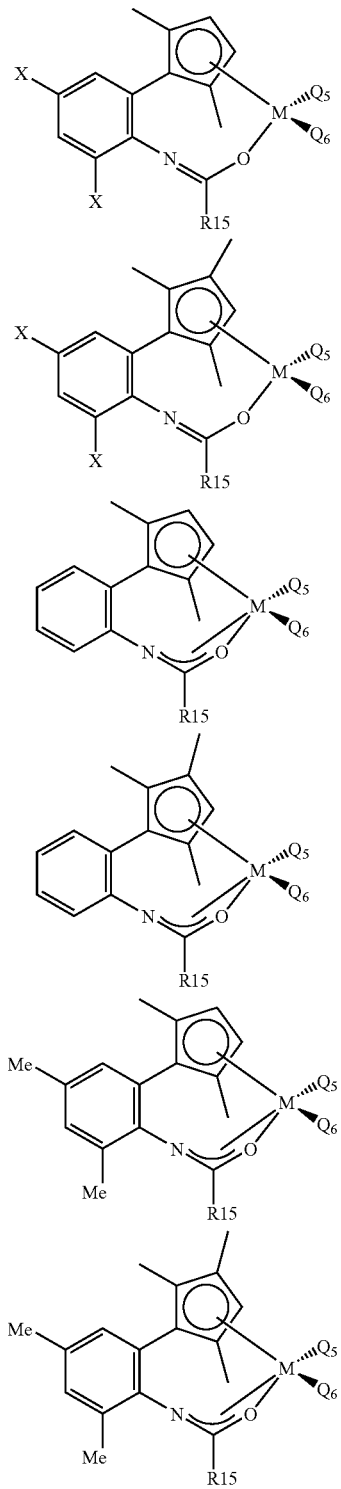

where $R_{15}$ is a methyl, t-butyl, or t-butoxy radical, and $Q_5$ and $Q_6$ are described above, and X is a halogen radical.

The present invention also provides amine-based compounds of Formulae 4 through 7 that are ligands coordinated with metal in the transition metal complex of Formulae 1 through 3:

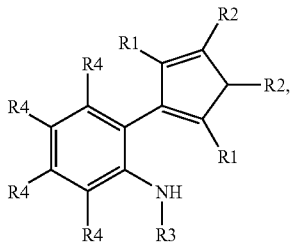

(4)

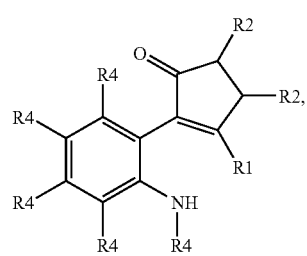

(5)

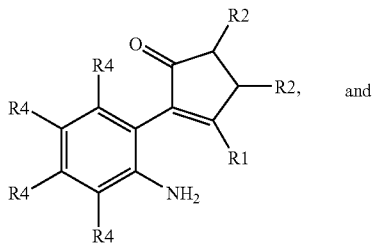

and (6)

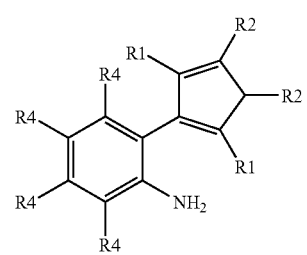

(7)

where $R_1$, $R_2$, $R_3$ and $R_4$ are described above. When these ligands are coordinated with metal, a phenylene bridge is formed and nitrogen and cyclopentadiene are coordinated with metal. These compounds of Formulae 4 through 7 may be used as a ligand of a transition metal complex. However, use of the compounds is not limited thereto. That is, the compounds can be used in any applications.

The present invention also provides an organic ketone-based boronic acid compound of Formula 8 that is used as an intermediate when the ligands described above are synthesized:

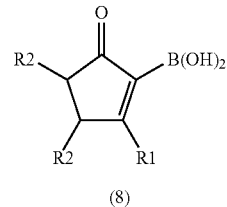

<Formula 8>

(8)

where $R_1$ and $R_2$ are described above.

A method of preparing transition metal complexes of Formulae 1 through 3 according to an embodiment of the present invention will now be described in detail. In order to obtain a novel monocyclopentadienyl ligand in which phenylene of Formula 4 acts as a bridge, a substituted boronic acid is reacted with an aniline compound in the presence of Pd metal catalyst by carbon-carbon coupling, which is Suzuki Reaction. The Suzuki Reaction is well known in the organic chemistry to form a C—C bond, and can be used to synthesize a monocyclopentadienyl ligand of Formula 4 in which various substituents are introduced to cyclopentadienyl, nitrogen, and a phenylene bridge. Ultimately, the transition metal complex of Formula 1 in which electronic and steric hindrance is controlled in the vicinity of metal can be synthesized.

Particularly, the method of synthesizing transition metal complexes represented by Formulae 1 through 3 includes: a) synthesizing a compound of Formula 6 by reacting a boronic acid compound of Formula 8 with a 2-bromoaniline compound of Formula 9; b) synthesizing a compound of Formula 5 by the compound of Formula 6 with $R_3X$ where X is a halogen atom; c) synthesizing a compound of Formula 4 by reacting a compound of Formula 5 with $R_1Li$ and then adding an acid thereto; and d) synthesizing a complex of Formula 1 or Formula 2 by reacting the compound of Formula 4 with the compound of Formula 10 and then adding $(CH_3)_nSiX_{4-n}$ where X is a halogen atom and n is 0, 1, 2, or 3 thereto:

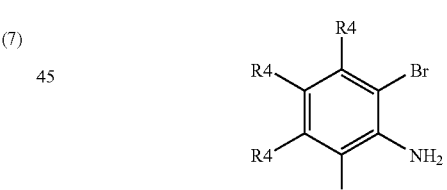

(9)

where $R_4$ is described above; and $$M(N(R_6)_2)_4 \quad (10)$$

where M is a transition metal of Group 4, and $R_6$ is a C1-C20 alkyl or aryl radical.

In operation (a), the boronic acid compound of Formula 8 can be obtained by reacting an unsaturated keton compound with a boron triester compound in a solvent of THF or ether and then adding an acid thereto, and the boronic acid compound of Formula 8 is reacted with a bromoaniline compound in the presence of a palladium catalyst via Suzuki Coupling reaction to form an amine-based compound of Formula 6. The palladium catalyst used can be a phosphine-based complex of Formula 11 which is well known. For example, the palladium catalyst is tetrakis(triphenylphosphine)palladium.

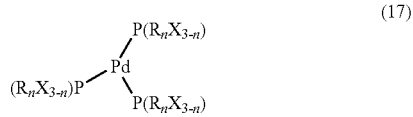 (17)

where R is alkyl or aryl; and X is a halogen atom.

In operation (b), a compound of Formula 6 is reacted with $R_3$—X where X is a halogen atom in the presence of an amine-based base, such as pylidine or triethylamine so that an acid such as H—X is removed and a compound of Formula 5 can be obtained. In the $R_3$—X, $R_3$ is selected from a C1-C20 alkyl sulfonyl or aryl sulfonyl radical, a C1-C20 alkyl carbonyl or aryl carbonyl radical, a C1-C20 alkyl carboxy or aryl carboxy radical, and a C1-C20 alkyl phosphonyl or aryl phosphonyl radical, and is preferably selected from methylsulfonyl, toluenesulfonyl, mesitylsulfonyl, and t-butylcarbonyl.

In operation (c), a compound of Formula 5 is reacted with an $R_1Li$ compound at low temperature and then an acid treatment is performed, thereby obtaining a compound of Formula 4. In order to increase the reactivity of the $R_1Li$ compound, the $R_1Li$ compound can be used together with a metal Lewis acid such as $CeCl_3$. In the $R_1Li$ compound, $R_1$ is selected from a C1-C20 alkyl or aryl; a C1-C20 alkenyl, alkylaryl, or arylalkyl; and a metalloid radical of Group 14 metal substituted with hydrocarbyl, preferably is a C1-C10 alkyl or aryl radical, and more preferably is selected from methyl, t-butyl, phenyl, benzyl, and (trimethyl)silylmethyl.

In operation (d), the monocyclopentadienyl ligand of Formula 4 prepared above is reacted with a Group 4 metal amino compound of Formula 10, and then $(CH_3)_nSiX_{4-n}$ where X is halogen and n is 0, 2, or 3 is added thereto, thereby obtaining Group 4 transition metal complexes of Formulae 1 through 3 according to the ligand structure change. The Group 4 metal amino compound is selected from tetrakis(dimethylamino) titanium, tetrakis(diethylamino)titanium, tetrakis(dimethylamino)zirconium, tetrakis(diethylamino)zirconium, tetrakis (dimethylamino)hafnium, and tetrakis(diethylamino) hafnium, and preferably selected from tetrakis (dimethylamino)titanium, tetrakis(dimethylamino) zirconium, and tetrakis(dimethylamino)hafnium. The reaction temperature of the monocyclopentadienyl ligand with the Group 4 metal amino compound may be in the range of 30° C.-150° C., preferably 50° C.-120° C., and more preferably 50° C.-100° C. The reaction time of the monocyclopentadienyl ligand with the Group 4 metal amino compound may be in the range of 6-168 hours, preferably 10-72 hours, and more preferably 12-48 hours. When the reaction temperature is less than 30° C., the ligand is insufficiently reacted with the metal amino compound and thus the yield and purity of the reaction product decrease. When the reaction temperature is higher than 150° C., the reaction product is thermally unstable and thus the yield and purity of the reaction product decreases. When the reaction time is shorter than 6 hours, the ligand is insufficiently reacted with the metal amino compound, whereas when the reaction time is longer than 168 hours, the obtained products may be changed into a different metal compound. In operation (d), the silane compound may be selected from chlorotrimethylsilane, dichlorodimethylsilane, trichloromethylsilane, and tetrachlorosilane. The mol ratio of the Group 4 metal compound that will react to the silane compound may be in the range of 1:1 to 1:5, and preferably 1:2 to 1:3. When the mol ratio of the Group 4 metal compound to the silane compound is less than 1:1, the chloride substitution occurs insufficiently and thus the yield and purity of the product decrease. On the other hand, when the mol ratio of the Group 4 metal compound to the silane compound is greater than 1:5, the obtained product can be changed into a different metal compound due to excess silane compound. In this case, however, excess silane compound may not affect significantly.

A method of preparing transition metal complexes of Formulae 1 through 3 according to another embodiment of the present invention includes: (a) synthesizing a compound of Formula 6 by reacting a boronic acid compound of Formula 8 with a 2-bromoaniline compound of Formula 9; (b) synthesizing a compound of Formula 7 by the compound of Formula 6 with $R_1Li$ and then adding an acid thereto; (c) synthesizing a compound of Formula 4 by reacting a compound of Formula 7 with $R_3X$ where X is a halogen atom; and (d) synthesizing a complex of Formula 1 or Formula 2 by reacting the compound of Formula 4 with the compound of Formula 10 and then adding $(CH_3)_nSiX_{4-n}$ where X is a halogen atom and n is 0, 1, 2, or 3 thereto. The present method is the same as the previous method, except that operation b and operation c of the previous method correspond to operation c' and operation b' of the present method, respectively. Respective operations of the present method is the same as in the previous method.

Methods of synthesizing the complex of Formula 1 may be represented by Reaction Scheme 1 or Reaction Scheme 2:

Reaction Scheme 1

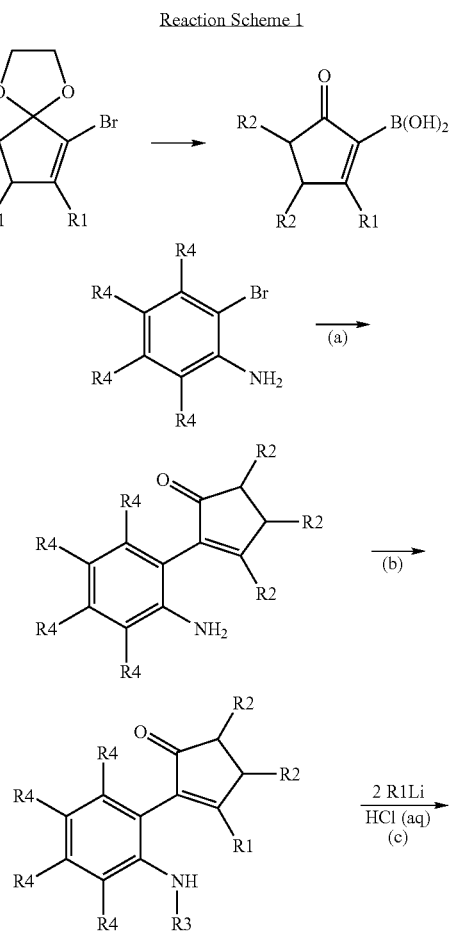

-continued

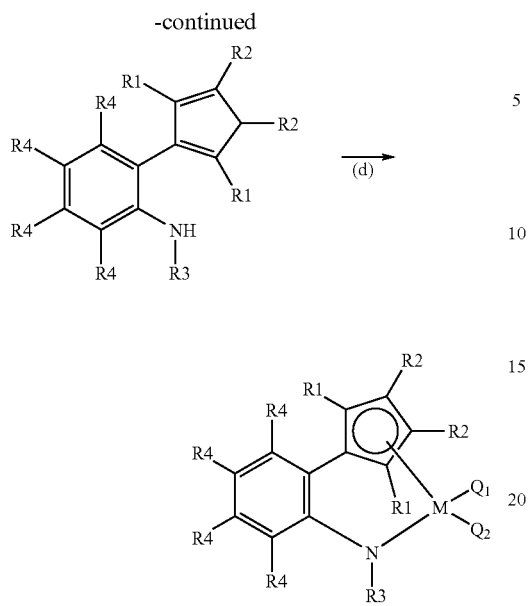

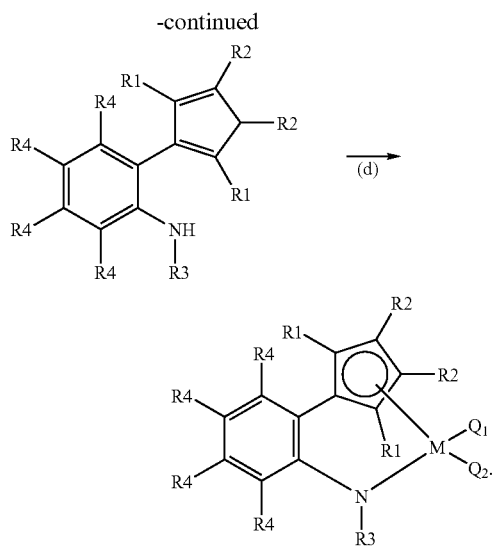

These Reaction Schemes can also be used to the complexes of Formula 2, and Formula 3.

Meanwhile, the complex of Formula 3 can be synthesized using other methods. For example, a method of synthesizing the complex of Formula 3 includes: e) synthesizing a dilithium form of the compound of Formula 7 by reacting a compound of Formula 7 with an alkyllithium that is a base; and f) synthesizing a complex of Formula 3 by reacting an in-situ mixtures composed of the dilithium compound, alkyllithium and $MX_4$ where X is halogen and M is a transition metal of Group 4, which is represented by Reaction Scheme 3:

Reaction Scheme 2

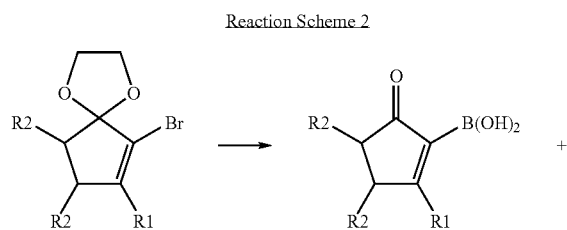

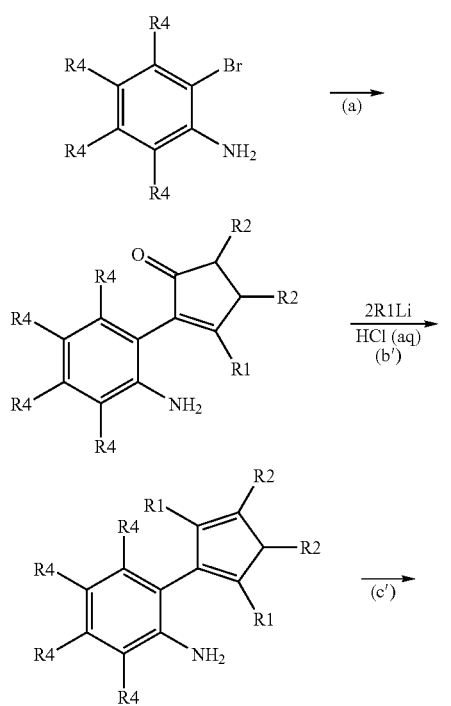

Reaction Scheme 3

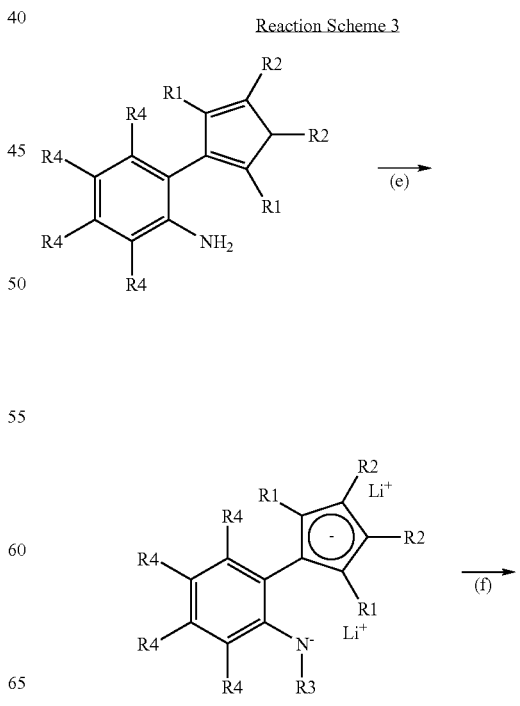

-continued

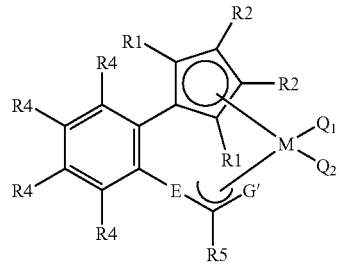

The Group 4 transition metal complex of Formula 3 can be easily synthesized using the method represented by Reaction Scheme 3, not using the Group 4 transition metal complex of Formula 10 and the silicon compound in operation (d) of the methods of synthesizing the complexes of Formula 1 through Formula 3. According to operation (e) of Reaction Scheme 3, in the presence of THF or diethylether, the ligand of Formula 7 is reacted with 2 eq. n-BuLi that is a strong base, thereby forming a dilithiated solid compound. According to operation (f), at a low temperature of −78° C., a Group 4 metal tetrachloride is reacted with 2 eq. alkyllithium compound, such as MeLi, thereby forming $Me_2MCl_2(solvent)_n$ where M is Ti or Zr, a solvent is THF or $Et_2O$, n is 1 or 2. And, the dilithium salt compound prepared in operation (e) reacts in-situ with the $Me_2MCl_2(solvent)_n$ to obtain the complex of Formula 3. When this method is used, the complex of Formula 3, in particular, a complex of Formula 3 where $Q_1$ and $Q_2$ are directly substituted with alkyl or aryl group can be obtained with a large yield (70% or more).

A catalyst composition according to an embodiment of the present invention including: a complex of one of Formulae 1 through 3, and at least one cocatalyst selected from compounds of Formula 11 through 13. The catalyst composition can be used for homopolymerization or copolymerization of olefin:

$$—[Al(R_7)—O]_a—$$ (11)

where $R_7$ is each independently a halogen radical; a C1-C20 hydrocarbyl radical; or a C1-C20 hydrocarbyl radical substituted with halogen, a is an integer of 2 or greater;

$$D(R_7)_3$$ (12)

where D is aluminum or boron, $R_7$ is described above; and $$[L—H]^+[Z(A)_4]^-, \text{ or } [L]^+[Z(A)_4]^-$$ (13)

where L is a neutral or cationic Lewis acid, H is a hydrogen atom; Z is an element of Group 13; and A is each independently a C6-C20 aryl or alkyl radical in which at least one hydrogen atom is substituted with halogen or a C1-C20 hydrocarbyl, alkoxy, or penoxy radical.

A method of preparing the catalyst composition according to an embodiment of the present invention include contacting the transition metal complex with the compound of Formula 11 or Formula 12 to obtain a mixture, and adding a compound of Formula 13 to the mixture. A method of preparing the catalyst composition according to another embodiment of the present invention includes contacting the transition metal complex with the compound of Formula 11.

In the former method of preparing a catalyst composition, the mole ratio of the transition metal complex to the compound of Formula 11 or Formula 12 may be in the range of 1:2 to 1:5,000, preferably 1:10 to 1:1,000, and preferably 1:20 to 1:500, and the mole ratio of the transition metal complex to the compound of Formula 13 may be in the range of 1:1 to 1:25, preferably 1:1 to 1:10, and most preferably 1:2 to 1:5. When the mole ratio of the transition metal complex to the compound of Formula 11 or Formula 12 is less than 1:2, the amount of the alkylating agent is so small that the metal compound is insufficiently alkylated. On the other hand, the mole ratio of the transition metal complex to the compound of Formula 11 or Formula 12 is greater than 1:5,000, the metal compound is alkylated, but excess alkylating agent can react with the activator of Formula 13 so that the alkylated metal compound is less activated. When the mole ratio of the transition metal complex to the compound of Formula 13 is less than 1:1, the amount of the activator is relatively small so that the metal compound is less activated. On the other hand, when the ratio of the transition metal complex to the compound of Formula 13 is greater than 1:25, the metal compound may be completely activated but excess activator remains, that is, the preparation process for the catalyst composition is expensive, and the obtained polymer purity is poor.

In the latter method of preparing the catalyst composition, the mol ratio of the transition metal complex to the compound of Formula 11 may be in the range of 1:10 to 1:10,000, preferably 1:100 to 1:5,000, and most preferably 1:500 to 1:2,000. When the mole ratio of the transition metal complex to the compound of Formula 11 is less than 1:10, the amount of the compound of Formula 11 is relatively small so that the transition metal complex is less activated and the obtained catalyst composition has low activity. On the other hand, when the mole ratio of the transition metal complex to the compound of Formula 11 is greater than 1:10,000, the metal compound is completely activated but excess activator remains, that is, the preparation process for the catalyst composition is expensive, and the obtained polymer purity is poor.

The reaction solvent used to preparing the activated catalyst composition can be a hydrocarbon based solvent, such as pentane, hexane, and heptane, or an aromatic solvent, such as benzene and toluene. The transition metal complexes of Formulae 1 through 3 and the cocatalysts can be supported by silica or alumina for use.

Examples of the compound of Formula 11 may include methylaluminoxane, ethylaluminoxane, isobutylaluminoxane, butylaluminoxane etc. For example the compound of Formula 11 is methylaluminoxane.

Examples of the alkyl metal compound of Formula 12 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminmethoxide, trimethylboron, triethylboron, triisobutylboron, tripropylboron, tributylboron etc. For example, the alkyl metal compound of Formula 12 is trimethylaluminum, triethylaluminum, or triisobutylaluminum.

Examples of the compound of Formula 13 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylanilinium tetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenyl boron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylamoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron etc.

A method of preparing a homopolymer or copolymer of polyolefin according to an embodiment of the present invention includes contacting a catalyst composition that contains the complex of one of Formulae 1 through 3 and at least one compound selected from compounds of Formulae 11 through 13 with at least one olefin monomer.

A polymerization process using the catalyst composition may be a solution process, but when the catalyst composition is used together with an inorganic support, such as silica, the polymerization process can also be a slurry or vapor process.

The catalyst composition can be melted or diluted in a solvent suitable for olefin polymerization, before being used. The solvent can be a C5-C12 aliphatic hydrocarbon solvent, such as pentane, hexane, heptane, nonane, decane, or isomers of these; an aromatic hydrocarbon, such as toluene or benzene; or a hydrocarbon solvent that is substituted with a chloride atom, such as dichloromethane or chlorobenzene. The solvent used therein may be treated with a small amount of alkylaluminum to remove water or air, which acts as a catalyst poison. When needed, more cocatalysts such as alkylaluminium can be used for the same purpose.

Examples of an olefin based monomer that can be polymerized using the metal complexes and the cocatalysts may include ethylene, alpha-olefin, cyclic olefin etc. In addition, a diene or triene olefin-based monomer having at least two double bonds can be polymerized. In particular, the olefin-based monomer can be ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbonadiene, ethyllidenenorbonene, phenylnorbonene, vinylnorbonene, dicyclopentadiene, 1,4-butadiene, 1,5-pentadiene, 1,6-hexadiene, stylene, alpha-methylstylene, divinylbenzene, or 3-chloromethylstylene. In addition, at least two different monomers of these can be copolymerized. The catalyst composition according to an embodiment of the present invention is used to copolymerize ethylene and 1-octene having large steric hindrance at a high reaction temperature of 90° C. to thereby obtain a copolymer having high molecular weight but having a very low density less than 0.910 g/cc.

A monomer of the copolymer may include ethylene and at least one compound selected from propylene, 1-butene, 1-hexene, and 4-methyl-1-pentene, and 1-octene.

The present invention will be described in further detail with reference to the following examples. These examples are for illustrative purposes only and are not intended to limit the scope of the present invention.

Synthesis of Ligand and Metal Complex

Organic reagents and solvents were obtained from Aldrich Co., Inc. and Merck Co., Inc. and purified using a standard method. Each process for the synthesis was performed being isolated from air and moisture to improve reproducibility of experiments. The structure of compounds was identified using a 400 MHz nuclear magnetic resonance (NMR) and an X-ray spectrometer.

EXAMPLE 1

2-dihydroxyboryl-3-methyl-2-cyclopenten-1-one 44.80 g (204.49 mmol) of 2-bromo-3-methyl-2-cyclopenten-1-on ethylene ketal compound were mixed with 240 mL of THF, and then 82 mL(204.49 mmol) of n-BuLi (2.5M in hexane) was added thereto at −78° C. The resultant mixture was mixed at −78° C. for one hour. Then, 42.31 g (224.95 mmol) of boron triisopropylester was added to the reaction product and then mixed at −60° C. or less for one hour. The resultant mixture was further reacted at −50° C. for 30 minutes, and then 110 mL of 2 N HCl was added thereto and mixed for 10 minutes. Subsequently, the reaction product was loaded to a separating funnel, 200 mL of ethylacetate (E.A) was added thereto, and then an organic layer was extracted therefrom. 55 mL of ethyl acetate (E.A) was used twice to extract the organic layer. The collected organic layer was dried over $MgSO_4$ to remove water therein and filtered using a glass filter. The solvent contained in the dried product was removed using a rotary vacuum evaporator to obtain a solid product. The solid product was melted using 300 mL of E.A and then twice recrystallized at −30° C. The remaining organic layer was column chromatographed (hexane:E.A=1:1) to remove by-products, and then recrystallized (24.30 g, 85%)

$^1$H NMR ($CDCl_3$): =6.75(s, 2H, OH), 2.69-2.67 (m, 2H, $CH_2$), 2.51-2.49 (m, 2H, $CH_2$), 2.45 (s, 3H, $CH_3$); $^{13}$C {$^1$H} NMR ($CDCl_3$): =217.35, 193.42, 35.73, 35.12, 20.42

EXAMPLE 2

2-dihydroxyboryl-3,4-dimethyl-2-cyclopenten-1-one 2-dihydroxyboryl-3,4-dimethyl-2-cyclopenten-1-one was obtained in the same manner as in Example 1 using 2-bromo-3,4-dimethyl-2-cyclopenten-1-one ethylene ketal compound (86%).

$^1$H NMR ($CDCl_3$): δ 1.24 (d, J=3.6 Hz, 3H, $CH_3$), 2.09 (dd, J=19, 2.0 Hz, 1H, $CH_2$), 2.39 (s, 3H, $CH_3$), 2.72 (dd, J=19, 6.8 Hz, 1H, $CH_2$), 2.84-2.86 (m, 1H, CH), 7.29 (s, 2H, OH) ppm. $^{13}$C{$^1$H} NMR ($CDCl_3$): δ 18.01, 18.90, 40.76, 44.22, 197.08, 216.12 ppm.

EXAMPLE 3

2-(2-aminophenyl)-3-methyl-2-cyclopenten-1-one 4.00 g (28.584 mmol) of 2-dihydroxyboryl-3-methyl-2-cyclopenten-1-one compound, 0.30 g (0.260 mmol) of tetrakis(triphenylphosphine)palladium, 4.13 g (38.978 mmol) of sodium carbonate were loaded to 250 mL schlenk flask, and then 80 mL of degassing DME and 27 mL of $H_2O$ that had been purged with $N_2$ were added thereto using a syringe. 4.47 g (25.985 mmol) of 2-bromoaniline was added to the flask using a syringe and reacted at 90° C. for 12 hours.

Subsequently, the reaction product, 200 mL of ethylacetate, and 100 mL of $H_2O$ were added to a separating funnel. Then, the organic layer was extracted. Subsequently, 100 mL of ethylacetate was added to the aqueous liquid to extract an organic layer again. The organic layer was dried over $MgSO_4$ to remove water therein and then a rotary vacuum evaporator was used to remove the remaining solvent. Then, the resultant organic layer was column chromatographed (hexane:E.A=1:1) (3.55 g, 73%).

$^1$H NMR (CDCl$_3$): =7.12 (td, J=7.6 Hz, 1H, Ph), 6.89 (dd, J=7.6 Hz, 1H, Ph), 6.77 (td, J=7.6 Hz, 1H, Ph), 6.72 (dd, J=7.6 Hz, 1H, Ph), 3.72 (br s, 2H, NH$_2$), 2.71-2.68 (m, 2H, CH$_2$CP), 2.56-2.54 (m, 2H, CH$_2$CP), 2.08 (s, 3H, CH$_3$); $^{13}$C {$^1$H} NMR (CDCl$_3$): =207.84, 174.84, 144.60, 139.42, 130.44, 128.73, 118.13, 117.84, 116.30, 34.74, 32.13, 18.56

EXAMPLE 4

2-(2-amino-4-fluorophenyl)-3-methyl-2-cyclopenten-1-one 4.937 g (25.982 mmol) of 2-bromo-4-fluoroaniline, 4.00 g (28.584 mmol) of 5-methyl-1-cyclopenten-2-one boronic acid compound, 0.30 g (0.260 mmol) of tetrakis(triphenylphosphine)palladium, and 4.13 g (38.978 mmol) of sodium carbonate were loaded to 250 mL schlenk flask, and then 80 mL of degassing DME and 27 mL of $H_2O$ that had been purged with $N_2$ were added thereto using a syringe. The mixture was reacted at 90° C. for 12 hours. The work-up was the same as in Example 3 (3.84 g, 72%).

$^1$H NMR (CDCl$_3$): =6.83 (t, J=7.6 Hz, 1H, Ph), 6.48 (t, J=7.6 Hz, 1H, Ph), 6.43 (d, J=10.4 Hz, 1H, Ph), 3.82 (br s, 2H, NH$_2$), 2.73-2.71 (m, 2H, CH$_2$CP), 2.58-2.55 (m, 2H, CH$_2^{Cp}$), 2.09 (s, 3H, CH$_3$); $^{13}$C {$^1$H} NMR (CDCl$_3$): =207.93, 175.26, 168.18(d, J=242.6 Hz, PhC-F) 146.47(d, J=5.7 Hz, Ph), 138.76, 131.90(d, J=9.8 Hz, Ph), 113.71, 105.08(d, 22 Hz, Ph), 102.91 (d, 22 Hz, Ph), 34.79, 32.22, 18.63

EXAMPLE 5

2-(2-amino-5-fluorophenyl)-3-methyl-2-cyclopenten-1-one 4.46 g (21.44 mmol) of 2-bromo-4-fluoroaniline, 3.30 g (23.582 mmol) of 5-methyl-1-cyclopenten-2-one boronic acid compound, 0.204 g (0.177 mmol) of tetrakis(triphenylphosphine)palladium, and 3.41 g (32.173 mmol) of sodium carbonate were loaded to 250 mL schlenk flask, and then 66 mL of degassing DME and 22 mL of $H_2O$ that had been purged with $N_2$ were added thereto using a syringe. The mixture was reacted at 90° C. for 12 hours. The work-up was the same as in Example 3 (3.76 g, 79%).

$^1$H NMR (CDCl$_3$): =6.74(td, J=8.8 Hz, 1H, Ph), 6.45 (d, J=7.6 Hz, 1H, Ph), 3.65 (br s, 2H, NH$_2$), 2.71-2.69 (m, 2H, CH$_2^{Cp}$), 2.54-2.52 (m, 2H, CH$_2$CP), 2.07 (s, 3H, CH$_3$); $^{13}$C {$^1$H} NMR (CDCl$_3$): =207.05, 176.05, 155.17(d, J=12.9 Hz, Ph), 152.63 (dd, J=12.9 Hz, Ph), 150.11 (d, J=12.9 Hz, Ph), 137.79, 129.60(d, J=3.1 Hz, Ph), 120.43 (dd, J=12.9 Hz, Ph), 111.97 (dd, 1.8 Hz, 22 Hz, Ph), 103.00 (t, 22 Hz, Ph), 34.66, 32.28, 18.50

EXAMPLE 6

2-(2-amino-5-methylphenyl)-3-methyl-2-cyclopenten-1-one 1.607 g (8.031 mmol) of 2-bromo-4-methylaniline, 1.180 g (8.432 mmol) of 5-methyl-1-cyclopenten-2-one boronic acid compound, 0.093 g (0.080 mmol) of tetrakis(triphenylphosphine)palladium, and 1.277 g (12.047 mmol) of sodium carbonate were loaded to 250 mL schlenk flask, and then 24 mL of degassing DME and 8 mL of $H_2O$ that had been purged with $N_2$ were added thereto using a syringe. The mixture was reacted at 90° C. for 12 hours. The work-up was the same as in Example 3 (1.66 g, 96%).

$^1$H NMR (CDCl$_3$): =6.88(s, 1H, Ph), 6.60 (s, 1H, Ph), 3.49 (br s, 2H, NH$_2$), 2.74 ?? 2.72(m, 2H, CH$_2^{Cp}$), 2.60??2.58(m, 2H, CH$_2^{Cp}$), 2.24 (s, 3H, CH$_3$), 2.19 (s, 3H, CH$_3$), 2.10 (s, 3H, CH$_3$); $^{13}$C {$^1$H} NMR (CDCl$_3$): =207.97, 174.68, 140.18, 139.97, 131.04, 128.58, 126.96, 123.00, 117.56, 34.93, 32.19, 20.48, 18.71, 17.89

EXAMPLE 7

2-(2-(2-mesitylenesulfonyl)aminophenyl)-3-methyl-2-cyclopenten-1-one 0.500 g (2.67 mmol) of 2-(2-aminophenyl)-3-methyl-2-cyclopenten-1-one, 0.253 g (3.204 mmol) of pyridine, 0.584 g (2.67 mmol) of 2-mesitylenesulfonyl chloride), and 2 mL of M.C (methylene chloride) were loaded to a 20 mL vial, and then reacted for 12 hours. 10 mL of M.C and 4 mL of 2 N HCl were added to the reaction product. The resultant organic layer is collected and then dried over $MgSO_4$ to remove water. The solvent contained in the dried product was removed using a rotary vacuum evaporator. The obtained solid was washed with 10 mL of diethyl ether and filtered using a glass filter. The filtered product was dried in vacuum to remove the solvent that had remained therein (0.790 g, 80%).

$^1$H NMR (CDCl$_3$): =7.51(d, J=7.6 Hz, 1H, Ph), 7.22 (t, J=7.6 Hz, 1H, Ph), 7.07 (t, J=7.6 Hz, 1H, Ph), 6.96 (d, J=7.6 Hz, 1H, Ph), 6.83 (s, 2H, Ph$^{Mes}$), 6.77 (s, 1H, NH), 2.44-2.40 (m, 4H, CH$_2$*2), 2.42 (s, 6H, Ph$^{Mes}$), 2.36 (s, 3H, Ph$^{Mes}$), 1.76 (s, 3H, CH$_3$).

EXAMPLE 8

2-(2-(2-mesitylenesulfonyl)amino-4-fluorophenyl)-3-methyl-2-cyclopenten-1-one 0.800 g (3.90 mmol) of 2-(2-amino-4-fluorophenyl)-3-methyl-2-cyclopenten-1-one, 0.339 g (4.29 mmol) of pyridine, 0.938 g (4.29 mmol) of 2-mesitylenesulfonyl chloride, and 4 mL of M.C were loaded to a 20 mL vial, and then reacted for 12 hours. The work-up was the same as in Example 7 (1.29 g, 85%).

$^1$H NMR (CDCl$_3$): =7.84(s, 1H, NH), 7.19 (d, J=6.0 Hz, 1H, Ph), 6.90 (m, 2H, Ph), 6.84 (s, 2H, Ph$^{Mes}$), 2.54-2.46 (m, 4H, CH$_2^{Cp}$*2), 2.09 (s, 3H, CH$_3$), 2.39 (s, 6H, Ph$^{Mes}$), 2.28 (s, 3H, Ph$^{Mes}$), 1.80 (s, 3H, CH$_3$); $^{13}$C {$^1$H} NMR (CDCl$_3$): =208.89, 177.35, 163.41, 160.93, 141.81, 139.72, 138.26, 136.26, 134.87, 131.79, 131.72, 123.23, 114.95, 113.20, 34.63, 32.81, 23.31, 20.92, 18.57

EXAMPLE 9

2-(2-(2-mesitylenesulfonyl)amino-5-fluorophenyl)-3-methyl-2-cyclopenten-1-one 0.700 g (3.14 mmol) of 2-(2-amino-5-fluorophenyl)-3-methyl-2-cyclopenten-1-one, 0.273 g (3.45 mmol) of pyridine, 0.754 g (3.45 mmol) of 2-mesitylenesulfonyl chloride, and 3 mL of M.C were loaded to a 20 mL vial, and then reacted for 12 hours. The work-up was the same as in Example 7 (0.760 g, 60%).

$^1$H NMR (CDCl$_3$): =7.05(s, 1H, NH), 6.90 (s, 1H, Ph), 6.87 (s, 2H, Ph$^{Mes}$), 6.54 (d, J=7.6 Hz, 1H, Ph), 2.54-2.46 (m, 4H, CH$_2$$^{Cp}$*2), 2.42 (s, 6H, CH$_3$Ph$^{Mes}$), 2.31 (s, 3H, CH$_3$), 2.01 (s, 3H, CH$_3$); $^{13}$C {$^1$H} NMR (CDCl$_3$): =207.55, 177.49, 162.06, 159.63, 159.10, 141.71, 138.76, 137.87, 135.55, 133.99, 131.67, 112.72, 104.67, 34.70, 32.84, 23.40, 21.02, 18.83

EXAMPLE 10

2-(2-(2-mesitylenesulfonyl)amino-5-methylphenyl)-3-methyl-2-cyclopenten-1-one 0.700 g (3.25 mmol) of 2-(2-amino-5-methylphenyl)-3-methyl-2-cyclopenten-1-one, 0.283 g (3.58 mmol) of pyridine, 0.782 g (3.58 mmol) of 2-mesitylenesulfonyl chloride, and 3 mL of M.C were loaded to a 20 mL vial, and then reacted for 12 hours. The work-up was the same as in Example 7 (1.29 g, 85%).

$^1$H NMR (CDCl$_3$): =7.24(s, 1H, NH), 7.01 (s, 1H, Ph), 6.76 (s, 2H, Ph$^{Mes}$), 6.48 (s, 1H, Ph), 2.43-2.39 (m, 4H, CH$_2$$^{Cp}$*2), 2.41 (s, 3H, CH$_3$), 2.36 (s, 6H, Ph$^{Mes}$), 2.25 (s, 6H, PhCH$_3$*2), 1.92 (s, 3H, Ph$^{Mes}$); $^{13}$C {$^1$H} NMR (CDCl$_3$): =207.97, 174.68, 140.18, 139.97, 132.24, 131.58, 131.04, 130.15, 129.57, 128.58, 126.96, 123.00, 117.56, 34.93, 32.19, 23.09 20.48, 19.89, 18.71, 17.89

EXAMPLE 11

2-(2-(p-toluenesulfonyl)aminophenyl)-3-methyl-2-cyclopenten-1-one 0.815 g (4.35 mmol) of 2-(2-aminophenyl)-3-methyl-2-cyclopenten-1-one, pyridine 0.413 g (5.22 mmol), 0.829 g (5.22 mmol) of p-toluenesulfonyl chloride, and 4 mL of M.C were loaded to a 20 mL vial, and then reacted for 12 hours. The work-up was the same as in Example 7 (1.330 g, 89%).

$^1$H NMR (CDCl$_3$): =7.80(s, 1H, NH), 7.55 (d, 1H, Ph), 7.43 (d, J=8.0 Hz, 2H, Ph$^{Ts}$), 7.33 (t, 1H, Ph), 7.19 (t, 1H, Ph), 7.12 (d, J=8.0 Hz, 2H, Ph$^{Ts}$), 6.89 (d, 1H, Ph), 2.43-2.40 (m, 4H, CH$_2$$^{Cp}$*2), 2.36 (s, 3H, CH$_3$), 1.75 (s, 3H, CH$_3$); $^{13}$C {$^1$H} NMR (CDCl$_3$): =208.91, 177.40, 142.75, 138.71, 137.33, 134.29, 130.62, 129.09, 129.00, 127.78, 127.04, 126.52, 126.13, 34.52, 32.61, 21.42, 18.76

EXAMPLE 12

2-(2-(p-toluenesulfonyl)amino-5-fluorophenyl)-3-methyl-2-cyclopenten-1-one 0.700 g (3.14 mmol) of 2-(2-amino-5-fluorophenyl)-3-methyl-2-cyclopenten-1-one, 0.298 g (3.76 mmol) of pyridine, 0.598 g (3.76 mmol) of p-toluenesulfonyl chloride, and 3 mL of M.C were loaded to a 20 mL vial, and then reacted for 12 hours. The work-up was the same as in Example 7 (1.000 g, 85%).

$^1$H NMR (CDCl$_3$): =7.62(s, 1H, NH), 7.52 (s, 1H, Ph), 7.38 (d, J=8.0 Hz, 2H, Ph$^{Ts}$), 7.28 (s, 1H, Ph), 7.06 (d, J=8.0 Hz, 2H, Ph$^{Ts}$), 2.39-2.35 (m, 4H, CH$_2$$^{Cp}$*2), 2.25 (s, 3H, CH$_3$), 1.69 (s, 3H, CH$_3$); $^{13}$C {$^1$H} NMR (CDCl$_3$): =207.56, 175.29, 141.94, 138.54, 136.27, 134.38, 130.62, 128.95, 128.57, 127.57, 126.96, 126.43, 125.93, 34.54, 33.08, 22.06, 17.91

EXAMPLE 13

2-(2-(p-toluenesulfonyl)amino-5-methylphenyl)-3-methyl-2-cyclopenten-1-one 0.600 g (2.79 mmol) of 2-(2-amino-5-methylphenyl)-3-methyl-2-cyclopenten-1-one, 0.243 g (3.07 mmol) f pyridine, 0.858 g (3.07 mmol) of p-toluenesulfonyl chloride, and 3 mL of M.C were loaded to a 20 mL vial, and then reacted for 12 hours. The work-up was the same as in Example 7 (0.800 g, 78%).

$^1$H NMR (CDCl$_3$): =7.28(s, 1H, NH), 7.21 (d, J=8.0 Hz, 2H, Ph$^{Ts}$), 7.14 (s, 1H, Ph), 6.76 (d, J=8.0 Hz, 2H, Ph$^{Ts}$), 6.86 (s, 1H, Ph), 2.43-2.39 (m, 4H, CH$_2$$^{Cp}$*2), 2.41 (s, 3H, CH$_3$), 2.25 (s, 6H, PhCH$_3$*2), 1.92 (s, 3H, Ph$^{Ts}$); $^{13}$C {$^1$H} NMR (CDCl$_3$): =208.95, 172.54, 139.54, 139.95, 132.24, 131.58, 130.84, 130.55, 129.52, 129.47, 128.96, 122.84, 116.52, 34.85, 31.94, 22.86 20.25, 19.67, 17.57

EXAMPLE 14

2-(2-amino)phenyl-3,4-dimethyl-2-cyclopenten-1-one

Yellow oil was obtained in the same manner as in Example 3, using 4.000 g (25.984 mmol) of 2-dihydroxyboryl-3,4-dimethyl-2-cyclopenten-1-one, 3.443 g (32.497 mmol) of sodium carbonate, 0.751 g (0.650 mmol) of tetrakis(triphenylphosphine)palladium, and 3.725 g (21.653 mmol) of 2-bromoaniline (2.872 g, 66%).

$^1$H NMR (CDCl$_3$): δ 1.32(d, J=3.6 Hz, 3H, CH$_3$), 2.07 (s, 3H, CH$_3$), 2.19 (dd, J=18.4, 1.6 Hz, 1H, CH$_2$—H), 2.83 (dd, J=18.4, 6.4 Hz, 1H, CH$_2$—H), 2.86 (qd, J=6.4, 1.6 Hz, 1H, CH—H), 3.72 (br s, 2H, NH$_2$), 6.77 (dd, J=7.6, 1.6 Hz, 1H, Ph), 6.81 (td, J=7.6, 1.6 Hz, 1H, Ph), 6.91 (dd, J=7.6, 1.6 Hz, 1H, Ph), 7.15 (td, J=7.6, 1.6 Hz, 1H, Ph) ppm. $^{13}$C{$^1$H} NMR (CDCl$_3$): δ 16.39, 19.39, 37.97, 43.51, 116.60, 117.01, 118.16, 118.55, 128.97, 130.67, 144.45, 178.93, 207.02 ppm.

EXAMPLE 15

2-(2-amino-3,5-dimethyl)phenyl-3,4-dimethyl-2-cyclopenten-1-one

White solid was obtained in the same manner as in Example 3, using 3.459 g (22.465 mmol) of 2-dihydroxyboryl-3,4-dimethyl-2-cyclopenten-1-one, 2.976 g (28.076 mmol) of sodium carbonate, 0.649 g (0.562 mmol) of tetrakis(triphenylphosphine)palladium, and 3.745 g (18.718 mmol) of 2-bromo-4,6-dimethylaniline (3.161 g, 74%).

$^1$H NMR (CDCl$_3$): δ 1.32(d, J=3.6 Hz, 3H, CH$_3$), 2.04 (s, 3H, CH$_3$), 2.18 (s, 3H, CH$_3$), 2.20 (s, 1H, CH$_2$—H), 2.24 (s, 3H, CH$_3$), 2.82 (dd, J=18.4, 6.4 Hz, 1H, CH$_2$—H), 2.94 (qd, J=6.4, 1.6 Hz, 1H, CH—H), 3.48 (br s, 2H, NH$_2$), 6.60 (s, 1H, Ph), 6.88 (s, 1H, Ph) ppm. $^{13}$C{$^1$H} NMR (CDCl$_3$): δ 16.19, 17.76, 19.32, 20.37, 37.67, 43.45, 117.42, 122.79, 126.74, 128.44, 130.88, 140.02, 178.58, 106.85 ppm.

EXAMPLE 16

2-(2-amino-3,5-difluoro)phenyl-3,4-dimethyl-2-cyclopenten-1-one

White solid was obtained in the same manner as in Example 3, using 2.000 g (12.990 mmol) of 2-dihydroxyboryl-3,4-dimethyl-2-cyclopenten-1-one, 1.967 g (18.557 mmol) of sodium carbonate, 0.429 g (0.371 mmol) of tetrakis(triphenylphosphine)palladium, and 2.436 g (12.371 mmol) of 2-bromo-4,6-difluoroaniline (1.938 g, 76%).

$^1$H NMR (CDCl$_3$): δ 1.29(d, J=3.6 Hz, 3H, CH$_3$), 2.04 (s, 3H, CH$_3$), 2.15 (dd, J=18.8, 2.0 Hz, 1H, CH$_2$—H), 2.79 (dd, J=18.8, 14.4 Hz, 1H, CH$_2$—H), 2.93 (q, J=6.4 Hz, 1H, CH—H), 3.65 (br s, 2H, NH$_2$), 6.54 (d, J$_{H-F}$=8.8 Hz, 1H, Ph), 6.78 (t, J$_{H-F}$=8.8 Hz, 1H, Ph) ppm.

EXAMPLE 17

2-(2,5-dimethylcyclopenta-1,4-dienyl)phenyl(2-mesitylenesulfonyl)amine 0.645 g (1.746 mmol) of 2-(2-(2-mesitylenesulfonyl)aminophenyl)-3-methyl-2-cyclopenten-1-one and 12 mL of THF were loaded to a 50 mL flask, and then 2.30 mL (3.677 mmol) of MeLi (1.6 M in diethyl ether) was added thereto at −78° C. and stirred at the same temperature for two hours. The reaction product was stirred for 2 hours while the temperature was slowly raised. 10 mL of distilled water was added to the resultant reaction product and the THF contained therein was removed using a rotary vacuum evaporator. 10 mL of E.A and 5 mL of 2 N HCl were added to the reaction product from which the THF had been removed and strongly stirred for 3 minutes. Subsequently, the organic layer was collected from the stirred reaction product. 5 mL of E.A was twice added to the aqueous layer to obtain the organic layer. The collected organic layer was neutralized using 5 mL of NaHCO$_3$ and dried over MgSO$_4$ to remove water contained therein. The solvent contained in the dried product was removed using a rotary vacuum evaporator. The product was filtered using a column chromatography (hexane: E.A=10:1) (0.550 g, 88%).

$^1$H NMR (CDCl$_3$): =7.51(d, J=7.6 Hz, 1H, Ph), 7.22 (t, J=7.6 Hz, 1H, Ph), 7.07 (t, J=7.6 Hz, 1H, Ph), 6.96 (d, J=7.6 Hz, 1H, Ph), 6.83 (s, 2H, Ph$^{Mes}$), 6.77 (s, 1H, NH), 2.44 (m, 4H, CH$_2$*2), 2.46 (s, 6H, Ph$^{Mes}$), 2.46 (s, 3H, Ph$^{Mes}$), 1.76 (s, 3H, CH$_3$)

EXAMPLE 18

2-(2,5-dimethylcyclopenta-1,4-dienyl)-4-fluorophenyl(2-mesitylenesulfonyl)-amine 0.636 g (1.581 mmol) of CeCl$_3$ and 15 mL of THF were loaded to a 50 mL flask, and then 2.30 mL (3.677 mmol) of MeLi (1.6 M in diethyl ether) was added thereto at −78° C. 30 minutes after the resultant mixture turned yellow, 0.500 g (1.290 mmol) of 2-(2-(2-mesitylenesulfonyl)amino-4-fluorophenyl)-3-methyl-2-cyclopenten-1-one melted in 15 mL of THF was added to the flask using a syringe and stirred at −78° C. for 2 hours. The stirred product was stirred for one hour while the temperature was slowly raised. 8 mL of distilled water was added to the flask and the THF contained in the reaction product was removed using a rotary vacuum evaporator. 8 mL of E.A and 4 mL of 2 N HCl were added to the reaction product from which the THF had been removed, and then strongly stirred for 3 minutes. Subsequently, the organic layer was collected from the stirred reaction product. 4 mL of E.A was twice added to the aqueous liquid to obtain the organic layer. The collected organic layer was neutralized using 4 mL of NaHCO$_3$ and dried over MgSO$_4$ to remove water contained therein. CeCl$_3$ and MgSO$_4$ were removed using a glass filter and the solvent contained in the dried product was removed using a rotary vacuum evaporator. The product was filtered using a column chromatography (hexane:E.A=10:1) (0.360 g, 72%).

EXAMPLE 19

2-(2,5-dimethylcyclopenta-1,4-dienyl)-5-fluorophenyl(2-mesitylenesulfonyl)-amine 0.500 g (1.233 mmol) of 2-(2-(2-mesitylenesulfonyl)amino-5-fluorophenyl)-3-methyl-2-cyclopenten-1-one and 10 mL of THF were added to a 50 mL flask, and then 1.927 ml (3.083 mmol) of MeLi (1.6 M in diethyl ether) was added thereto at −78° C. and stirred at the same temperature for 2 hours. The reaction product was stirred for 2 hours while the temperature was slowly raised. The work-up was the same as in Example 17 (0.173 g, 35%).

$^1$H NMR (CDCl$_3$): =6.88(s, 2H, Ph$^{Mes}$), 6.84-6.81 (m, 1H, Ph), 6.64-6.61 (m, 1H, Ph), 6.09 (s, 1H, NH), 5.89 (s, 1H, CH$_2$$^{Cp}$), 2.85-2.84 (m, 2H, CH$_2$$^{Cp}$), 2.50 (s, 6H, CH$_3$*2), 2.31 (s, 3H, CH$_3$), 1.82 (s, 3H, CH$_3$), 1.68 (s, 3H, CH$_3$); $^{13}$C {$^1$H} NMR (CDCl$_3$): =142.94, 142.19, 141.97, 141.69, 138.84, 131.53, 125.36, 125.05, 112.78, 112.57, 103.70, 103.45, 103.20, 94.58, 44.53, 22.96, 21.02, 14.77, 14.77, 14.49

EXAMPLE 20

2-(2,5-dimethylcyclopenta-1,4-dienyl)-5-methylphenyl(2-mesitylenesulfonyl)-amine 0.500 g (1.258 mmol) of 2-(2-(2-mesitylenesulfonyl)amino-5-methylphenyl)-3-methyl-2-cyclopenten-1-one and 10 mL of THF were added to a 50 mL flask at −78° C., and 1.965 ml (3.145 mmol) of MeLi (1.6 M in diethyl ether) was added thereto. The following experiment was the same as in Example 17 (0.182 g, 37%).

$^1$H NMR (CDCl$_3$): =7.03(s, 1H, Ph), 6.80 (s, 2H, Ph$^{Mes}$), 6.65 (s, 1H, Ph), 6.13 (s, 1H, NH), 5.77 (s, 1H, CH$_2$$^{Cp}$), 2.79-2.60 (m, 2H, CH$_2$$^{cp}$), 2.43 (s, 3H, CH$_3$), 2.36 (s, 6H, CH$_3$$^{mes}$), 2.31 (s, 3H, CH$_3$), 2.29 (s, 3H, CH$_3$), 1.70 (s, 3H, CH$_3$), 1.50 (s, 3H, CH$_3$); $^{13}$C {$^1$H} NMR (CDCl$_3$): =142.41, 141.45, 140.08, 139.69, 138.78, 137.40, 136.41, 134.38, 131.51, 131.36, 130.98, 128.76, 128.45, 124.71, 44.14, 23.43, 23.09, 21.05, 20.96, 19.89, 14.71, 14.54

EXAMPLE 21

2-(2,3,5-trimethylcyclopenta-1,4-dienyl)phenylamine

Brown solid was obtained in the same manner as in Example 18 using 9.598 g (38.973 mmol) of anhydrous CeCl$_3$, 24.358 mL (38.973 mmol) of MeLi (1.6 M in diethyl ether), and 2.615 g (12.991 mmol) of 2-(2-amino)phenyl-3,4-dimethyl-2-cyclopenten-1-one (2.307 g, 89%).

$^1$H NMR (CDCl$_3$): δ 1.56(s, 3H, Cp—CH$_3$), 1.75 (s, 3H, Cp—CH$_3$), 1.85 (s, 3H, Cp—CH$_3$), 2.82 (s, 2H, Cp—CH$_2$), 3.55 (br s, 2H, NH$_2$), 6.62 (dd, J=7.6, 1.6 Hz, 1H, Ph), 6.65 (td, J=7.6, 1.6 Hz, 1H, Ph), 6.82 (dd, J=7.6, 1.6 Hz, 1H, Ph), 6.99 (td, J=7.6, 1.6 Hz, 1H, Ph) ppm. $^{13}$C{$^1$H} NMR (CDCl$_3$): δ 11.67, 13.63, 14.35, 48.80, 114.67, 117.76, 122.79, 127.69, 130.13, 133.14, 135.54, 136.73, 139.61, 144.14 ppm.

EXAMPLE 22

2-(2,3,5-trimethylcyclopenta-1,4-dienyl)-4,6-dimethylphenylamine

Yellow solid was obtained in the same manner as in Example 18 using 9.666 g (39.246 mmol) of anhydrous $CeCl_3$, 24.529 mL (39.246 mmol) of MeLi (1.6 M in diethyl ether), and 3.000 g (13.082 mmol) of 2-(2-amino-3,5-dimethyl)phenyl-3,4-dimethyl-2-cyclopenten-1-one (2.241 g, 75%).

$^1$H NMR ($CDCl_3$): δ 1.74(s, 3H, Cp—$CH_3$), 1.93 (s, 3H, Cp—$CH_3$), 2.04 (s, 3H, Cp—$CH_3$), 2.26 (s, 3H, Ph-$CH_3$), 2.33 (s, 3H, Ph-$CH_3$), 3.00 (q, J=2.4 Hz, 2H, Cp—$CH_2$), 3.47 (br s, 2H, $NH_2$), 6.72 (s, 1H, Ph), 6.91 (s, 1H, Ph) ppm. $^{13}$C{$^1$H} NMR ($CDCl_3$): δ 11.72, 13.61, 14.40, 17.88, 20.55, 48.78, 121.78, 122.61, 126.21, 128.20, 129.60, 133.00, 135.66, 136.41, 139.85, 140.07 ppm.

EXAMPLE 23

2-(2,3,5-trimethylcyclopenta-1,4-dienyl)-4,6-fluorophenylamine

Yellow oil was obtained in the same manner as in Example 18 using (4.120 g, 16.730 mmol) of anhydrous $CeCl_3$, 29.206 mL (16.730 mmol) of MeLi (1.6 M in diethyl ether), and 1.300 g of (5.577 mmol) 2-(2-amino-3,5-difluoro)phenyl-3,4-dimethyl-2-cyclopenten-1-one (0.902 g, 70%).

$^1$H NMR ($CDCl_3$): δ 1.67(s, 3H, Cp—$CH_3$), 1.87 (s, 3H, Cp—$CH_3$), 1.97 (s, 3H, Cp—$CH_3$), 3.96 (br s, 2H, Cp—$CH_2$), 3.53 (br s, 2H, $NH_2$), 6.52 (d, $J_{H-F}$=8.8 Hz, 1H, Ph), 6.76 (t, $J_{H-F}$=8.8 Hz, 1H, Ph) ppm. $^{13}$C{$^1$H} NMR ($CDCl_3$): δ 11.58, 13.60, 14.35, 48.95, 102.08, 111.67, 125.30, 128.98, 133.85, 134.76, 137.83, 137.96, 149.46, 151.96, 152.84, 155.19 ppm.

EXAMPLE 24 phenylene(2-mesitylenesulfonylamido)(2,5-dimethylcyclopentadienyl)titanium bis(dimethylamide)

0.200 g (0.544 mmol) of 2-(2,5-dimethylcyclopenta-1,4-dienyl)phenyl(2-mesitylene-sulfonyl)amine melted in 4 mL of toluene and 0.122 g (0.544 mmol) of Ti($NMe_2$)$_4$ diluted in 3 mL of toluene were loaded to a 25 mL flask, and then reacted at 50° C. for 12 hours. Toluene and dimethylamine contained in the reaction product was removed in vacuum. The resultant product was solidated using pentane.

$^1$H NMR ($CDCl_3$): =7.19(d, J=7.6 Hz, 1H, Ph), 7.08 (t, J=7.6 Hz, 1H, Ph), 6.98 (t, J=7.6 Hz, 1H, Ph), 6.91 (d, J=7.6 Hz, 1H, Ph), 6.58 (s, 2H, Ph$^{Mes}$), 5.69 (s, 1H, $CH_2^{Cp}$), 3.24 (s, 12H, N—$CH_3$), 2.64 (s, 6H, $CH_3$*2), 2.08 (s, 3H, $CH_3$) 1.74 (s, 6H, $CH_3$*2)

EXAMPLE 25

5-fluorophenylene(2-mesitylenesulfonylamido)(2,5-dimethylcyclopentadienyl)titanium bis(dimethylamide)

The same experiment as in Example 24 was carried out, using 0.160 g (0.415 mmol) of 2-(2,5-dimethylcyclopenta-1,4-dienyl)-5-fluorophenyl(2-mesitylenesulfonyl)amine and 0.093 g (0.415 mmol) of Ti($NMe_2$)$_4$.

$^1$H NMR($C_6D_6$): =7.12(d, J=8.0 Hz, 1H, Ph), 6.71 (t, J=8.0 Hz, 1H, Ph), 6.57 (s, 2H, Ph$^{Mes}$), 6.46 (td, J=8.0 Hz, 1H, Ph), 5.70 (s, 2H, $CH_2^{Cp}$), 3.27 (s, 12H, N—$CH_3$), 2.67 (s, 6H, $CH_3$*2), 1.87 (s, 3H, $CH_3$) 1.76 (s, 6H, $CH_3$*2)

EXAMPLE 26

4-fluorophenylene(2-mesitylenesulfonylamido)(2,5-dimethylcyclopentadienyl)titanium bis(dimethylamide)

The same experiment as in Example 24 was carried out, using 0.158 g (0.392 mmol) of 2-(2,5-dimethylcyclopenta-1,4-dienyl)-4-fluorophenyl(2-mesitylenesulfonyl)amine and 0.093 g (0.415 mmol) of Ti($NMe_2$)$_4$.

$^1$H NMR($C_6D_6$): =6.69(s, 2H, Ph$^{Mes}$), 6.66-6.63 (m, 1H, Ph), 6.52-6.47 (m, 1H, Ph), 5.76 (s, 2H, $CH_2^{Cp}$), 3.15 (s, 12H, N—$CH_3$), 2.92 (s, 6H, $CH_3$*2), 1.96 (s, 6H, $CH_3$*2), 1.95 (s, 3H, $CH_3$); $^{13}$C {$^1$H} NMR($C_6D_6$): =140.50, 137.94, 131.63, 123.78, 112.60, 112.57, 112.39, 112.35, 112.21, 104.65, 104.41, 104.15, 51.36, 23.33, 23.30, 20.85, 13.88

EXAMPLE 27

4-methylphenylene(2-mesitylenesulfonylamido)(2,5-dimethylcyclopentadienyl)titanium bis(dimethylamide)

0.172 g (0.435 mmol) of 2-(2,5-dimethylcyclopenta-1,4-dienyl)-4-methylphenyl(2-mesitylenesulfonyl)amine and 0.093 g (0.415 mmol) of Ti($NMe_2$)$_4$ were reacted at 80° C. Toluene and dimethylamine was removed from the reaction product in vacuum. The resultant reaction product was solidated using pentane.

EXAMPLE 28

2-(2,5-dimethylcyclopenta-1,4-dienyl)phenyl(p-toluenesulfonyl)amine

The same experiment as in Example 17 was carried out, using 1.000 g (2.93 mmol) of 2-(2-(p-toluenesulfonyl)aminophenyl)-3-methyl-2-cyclopenten-1-one and 3.660 ml (5.860 mmol) of MeLi (1.6 M in diethyl ether) (0.617 g, 62%).

$^1$H NMR ($CDCl_3$): =7.66(d, J=7.6 Hz, 1H, Ph), 7.59 (d, J=7.6 Hz, 2H, Ph$^{Ts}$), 7.21 (t, J=7.6 Hz, 1H, Ph), 7.15 (d, J=7.6 Hz, 2H, Ph$^{Ts}$), 7.02 (t, J=7.6 Hz, 1H, Ph), 6.90 (d, J=7.6 Hz, 1H, Ph), 6.64 (s, 1H, NH), 5.93 (s, 1H, $CH^{Cp}$), 3.09-2.85 (m, 2H, $CH_2$), 2.36 (s, 3H, $CH_3$), 1.67 (s, 3H, $CH_3$), 1.38 (s, 3H, $CH_3$); $^{13}$C {$^1$H} NMR ($CDCl_3$): =143.57, 142.00, 142.16, 137.32, 134.07, 134.55, 129.90, 129.32, 129.12, 127.95, 126.95, 125.38, 123.59, 118.11, 44.50, 21.46, 14.36, 14.05

EXAMPLE 29

2-(2,5-dimethylcyclopenta-1,4-dienyl)-4-fluorophenyl(p-toluenesulfonyl)amine

The same experiment as in Example 17 was carried out, using 1.000 g (2.93 mmol) of 2-(2-(p-toluenesulfonyl)amino-4-fluorophenyl)-3-methyl-2-cyclopenten-1-one and 3.660 ml (5.860 mmol) of MeLi (1.6 M in diethyl ether) (0.210 g, 53%).

$^1$H NMR ($CDCl_3$): =7.62(d, J=8.0 Hz, 2H, Ph$^{Ts}$), 7.20 (d, J=8.0 Hz, 2H, Ph$^{Ts}$), 6.81-6.76 (m, 1H, Ph), 6.66-6.63 (m, 1H, Ph), 6.45 (s, 1H, NH), 5.87 (d, J=1.6 Hz, 1H, $CH^{Cp}$), 2.87-2.72 (m, 2H, $CH_2$), 2.42 (s, 3H, $CH_3$), 1.82 (s, 3H, $CH_3$), 1.72 (d, J=2.0 Hz, 3H, $CH_3$); $^{13}$C {$^1$H} NMR ($CDCl_3$): =161.36, 159.38, 158.89, 156.79, 143.05, 142.65, 141.84, 137.36, 128.93, 126.64, 124.79, 118.94, 112.73, 103.09, 44.30, 21.45, 14.69, 14.44

EXAMPLE 30 phenylene(p-toluenesulfonylamido)(2,5-dimethylcyclopentadienyl)titanium bis(dimethylamide)

The same experiment as in Example 17 was carried out, using 0.500 g (1.473 mmol) of 2-(2,5-dimethylcyclopenta-1,4-dienyl)phenyl(p-toluenesulfonyl)amine, and 0.330 g (1.473 mmol) of Ti(NMe$_2$)$_4$. The crystalline structure of the product is shown in FIG. 1.

$^1$H NMR(C$_3$D$_3$): =8.12(d, J=8.0 Hz, 1H, Ph), 7.80 (d, J=7.6 Hz, 2H, Ph$^{Ts}$), 7.14 (t, J=8.0 Hz, 1H, Ph), 6.97 (d, J=8.0 Hz, 1H, Ph), 6.84 (t, J=8.0 Hz, 1H, Ph), 6.74 (d, J=8.0 Hz, 2H, Ph$^{Ts}$), 5.74 (s, 2H, CH$^{Cp}$), 3.28 (s, 12H, N—CH$_3$), 1.86 (s, 3H, CH$_3$), 1.67 (s, 6H, CH$_3$*2)

EXAMPLE 31

4-fluorophenylene(p-toluenesulfonylamido)(2,5-dimethylcyclopentadienyltitanium bis(dimethylamide)

The same experiment as in Example 24 was carried out, using 0.146 g (0.389 mmol) of 2-(2,5-dimethylcyclopenta-1,4-dienyl)-4-fluorophenyl(p-toluenesulfonyl)amine, and 0.087 g (0.389 mmol) of Ti(NMe$_2$)$_4$.

$^1$H NMR(C$_3$D$_3$): =8.22(d, J=8.0 Hz, 2H, Ph$^{Ts}$), 6.87 (d, J=8.0 Hz, 2H, Ph$^{Ts}$), 6.65 (d, J=7.6 Hz, 1H, Ph), 6.50 (t, J=7.6 Hz, 1H, Ph), 5.86 (s, 2H, CH$^{Cp}$), 3.28 (s, 12H, N—CH$_3$), 1.94 (s, 3H, CH$_3$), 1.89 (s, 6H, CH$_3$*2)

EXAMPLE 32 phenylene(2-mesitylenesulfonylamido)(2,5-dimethylcyclopentadienyl)titanium dichloride 0.200 g (0.426 mmol) of C6H$_4$(2,4,6-Me$_3$PhSO$_2$N)(2,5-Me$_2$Cp)Ti(NMe$_2$)$_2$ (in situ chlorinated after NMR measuring) melted in 3 mL of toluene and 0.211 g (1.634 mmol) of Me$_2$SiCl$_2$ diluted in 1 mL of toluene were loaded to a 20 mL vial, and then reacted for 1 hour. Toluene contained in the reaction product was removed in vacuum. The resultant product was solidated using pentane (0.190 g, 72%).

$^1$H NMR(C$_3$D$_3$): =6.84(m, 3H, Ph), 6.56 (s, 2H, CH$^{Cp}$), 6.54 (d, J=7.6 Hz, 1H, Ph), 6.52 (s, 2H, Ph$^{Mes}$), 2.60 (s, 6H, CH$_3$*2), 1.88 (s, 3H, CH$_3$), 1.82 (s, 6H, CH$_3$*2); $^{13}$C {$^1$H} NMR(C$_3$D$_3$): =155.58, 143.37, 143.22, 139.83, 139.32, 132.47, 129.78, 128.53, 126.20, 124.60, 124.04, 114.54, 23.61, 20.93, 15.04

EXAMPLE 33

5-fluorophenylene(2-mesitylenesulfonylamido)(2,5-dimethylcyclopentadienyl)titanium dichloride The same expresiment as in Example 32 was carried out, using 0.182 g of 5-FC$_6$H$_3$(2,4,6-Me$_3$PhSO$_2$N)(2,5-Me$_2$Cp)Ti(NMe$_2$)$_2$ (in situ chlorinated after NMR measuring) and 0.161 g (1.245 mmol) of Me$_2$SiCl$_2$. The product was measured by NM R spectroscopy, but was not identified.

EXAMPLE 34

4-fluorophenylene(2-mesitylenesulfonylamido)(2,5-dimethylcyclopentadienyl)titanium dichloride The same expresiment as in Example 32 was carried out, using 0.170 g of 4-FC$_6$H$_3$(2,4,6-Me$_3$PhSO$_2$N)(2,5-Me$_2$Cp)Ti(NMe$_2$)$_2$ (in situ chlorinated after NMR measuring) and 0.152 g (1.176 mmol) of Me$_2$SiCl$_2$. The product was measured by NMR spectroscopy, but was not identified.

EXAMPLE 35 phenylene(p-toluenesulfonylamido)(2,5-dimethylcyclopentadienyl)titanium dichloride The same expresiment as in Example 32 was carried out, using 0.150 g (0.317 mmol) of C6H$_4$(4-MePhSO$_2$N)(2,5-Me$_2$Cp)Ti(NMe$_2$)$_2$ and 0.123 g (0.951 mmol) of Me$_2$SiCl$_2$ (0.130 g, 88%).

$^1$H NMR(C$_3$D$_3$): =8.14(d, J=7.6 Hz, 2H, Ph$^{Ts}$), 7.09 (d, J=7.6 Hz, 2H, Ph), 6.94 (t, J=7.6 Hz, 1H, Ph), 6.80 (t, J=7.6 Hz, 1H, Ph), 6.74 (d, J=7.6 Hz, 1H, Ph), 6.61(d, J=7.6 Hz, 2H, Ph$^{Ts}$), 6.59 (s, 2H, CH$^{Cp}$), 1.75 (s, 6H, CH$_3$*2), 1.73.(s, 3H, CH$_3$)

EXAMPLE 36

4-fluorophenylene(p-toluenesulfonylamido)(2,5-dimethylcyclopentadienyl)titanium dichloride The same expresiment as in Example 32 was carried out, using 0.102 g (0.200 mmol) of 4-FC$_6$H$_4$(4-MePhSO$_2$N)(2,5-Me$_2$Cp)Ti(NMe$_2$)$_2$ and 0.077 g (0.601 mmol) of Me$_2$SiCl$_2$ (0.080 g, 81%).

$^1$H NMR(C$_3$D$_3$): =8.18(d, J=8.0 Hz, 2H, Ph$^{Ts}$), 6.73 (d, 1H, CH$^{Cp}$), 6.65 (d, J=8.0 Hz, 2H, Ph$^{Ts}$), 6.54 (d, 1H, CH$^{Cp}$), 6.27-6.21 (m, 1H, Ph), 6.14-6.12 (m, 1H, Ph), 1.84 (s, 3H, CH$_3$), 1.79 (s, 3H, CH$_3$), 1.66 (s, 3H, CH$_3$)

EXAMPLE 37

2-(2,5-dimethylcyclopenta-1,4-dienyl)phenyl(methanesulfonyl)amine 2-(2,5-dimethylcyclopenta-1,4-dienyl)phenylamine (0.500 g, 2.699 mmol) was melted in 5 mL of M.C, and then 0.235 g (2.969 mmol) of pyridine and 0.340 g (2.969 mmol) of methanesulfonyl chloride were added thereto. The reactants were reacted at room temperature for 7 hours. Then, 4 mL of 2 N HCl and 10 mL of M.C were added to the reaction product. The organic layer was collected and dried over MgSO$_4$ to remove water contained therein. The solvent contained in the resultant organic layer was removed using a rotary vacuum evaporator. The product was filtered using 10 mL of diethyl ether, thereby obtaining white solid (0.482 g, 68%).

$^1$H NMR (CDCl$_3$): δ 0.92 (d, J=1.6 Hz, 3H, CH$_3$), 1.89 (s, 3H, CH$_3$), 2.95 (s, 3H, CH$_3$), 2.99-3.13 (m, 2H, CH$_2$), 6.03 (d, J=1.6 Hz, 1H, CH), 6.45 (s, 1H, NH), 7.09 (dd, J=7.6, 1.6 Hz, 1H, Bz$^{3\ or\ 6}$), 7.15 (td, J=7.6, 1.2 Hz, 1H, Bz$^{4\ or\ 5}$), 7.33 (td, J=7.6, 1.6 Hz, 1H, Bz$^{4\ or\ 5}$), 7.63 (d, J=7.6 Hz, 1H, Bz$^{3\ or\ 6}$) ppm.

EXAMPLE 38 phenylene(methanesulfonylamido)(2,5-dimethylcyclopentadienyl)titanium bis(dimethylamide)

0.400 g (1.519 mmol) of 2-(2,5-dimethylcyclopenta-1,4-dienyl)phenyl (methanesulfonyl)amine and 0.341 g (1.519 mmol) of Ti(NMe$_2$)$_4$ were added to 12 mL of toluene, and then reacted at 50° C. for 12 hours. The solvent contained in the reaction product was removed in a reduced pressure. The resultant reaction product was filtered using 10 mL of pentane in a drybox and then dried in a reduced pressure, thereby obtaining red solid (0.507 g, 84%).

$^1$H NMR(C$_6$D$_6$): δ 1.63 (s, 6H, Cp—CH$_3$), 2.45 (s, 3H, CH$_3$), 3.11 (s, 12H, Ti(NMe$_2$)$_3$), 5.62 (s, 1H, CH), 6.94 (t, J=7.2 Hz, 1H, BZ$^{4\ or\ 5}$), 6.94 (d, J=7.2 Hz, 1H, BZ$^{3\ or\ 6}$), 7.16 (t, J=7.2 Hz, 1H, Bz$^{4\ or\ 5}$), 8.04 (d, J=7.2 Hz, 1H, Bz$^{3\ or\ 6}$) ppm.

EXAMPLE 39 phenylene(methanesulfonylamido)(2,5-dimethylcyclopentadienyl)titanium dichloride 0.400 g (1.007 mmol) of C6H$_4$(MeSO$_2$N)(2,5-Me$_2$Cp)Ti(NMe$_2$)$_2$ and 0.390 g (3.020 mmol) Me$_2$SiCl$_2$ were added to 10 mL of toluene and then reacted at room temperature for one hour. By-products contained in the reaction product was removed in a reduced pressure. The resultant reaction product was filtered using 10 mL of pentane in a drybox and dried in a reduced pressure (0.298 g, 78%).

$^1$H NMR(C$_6$D$_6$): δ 1.62 (broad s, 6H, Cp—CH$_3$), 2.51 (s, 3H, CH$_3$), 6.41-6.62 (broad s, 1H, CH), 6.75 (d, J=7.2 Hz, 1H, Bz$^{3\ or\ 6}$), 6.86 (t, J=7.2 Hz, 1H, Bz$^{4\ or\ 5}$), 7.01 (t, J=7.2 Hz, 1H, Bz$^{4\ or\ 5}$), 7.04 (d, J=7.2 Hz, 1H, Bz$^{3\ or\ 6}$)

EXAMPLE 40

2-(2,3,5-trimethylcyclopenta-1,4-dienyl)phenyl(p-toluenesulfonyl)amine 0.131 g (1.505 mmol) of pyridine and 0.316 g (1.656 mmol) of p-toluenesulfonyl chloride were added to 0.300 g (1.505 mmol) of 2-(2,3,5-trimethylcyclopenta-1,4-dienyl) phenylamine melted in 3 mL of MC, and then reacted at room temperature for 12 hours. 3 mL of 2 N HCl was added to the reaction product and strongly stirred for a few minutes. The organic layer was collected. The collected organic layer was neutralized with 3 mL of H$_2$O without delay and dried over MgSO$_4$. The product was filtered using a column chromatography with hexane/ethylacetate (v/v=3:1). The solvent contained in the purified product was dried in vacuum, thereby obtaining white solid (0.340 g, 64%).

$^1$H NMR (CDCl$_3$): δ 1.32(d, J=1.6 Hz, 3H, CH$_3$), 1.65 (s, 3H, CH$_3$), 1.95 (s, 3H, CH$_3$), 2.38 (s, 3H, CH$_3$), 2.95 (qd, J=19.2, 1.6 Hz, 2H, Cp—CH$_2$), 6.67 (s, 1H, NH), 6.92 (dd, J=7.6, 1.6 Hz, 1H, Ph), 7.05 (td, J=7.6, 1.6 Hz, 1H, Ph), 7.15 (d, J=8.0 Hz, 2H, Ts-Ph), 7.24 (td, J=7.6, 1.6 Hz, 1H, Ph), 7.62 (d, J=8.0 Hz, 2H, Ts-Ph), 7.64 (dd, J=7.6, 1.6 Hz, 1H, Ph) ppm. $^{13}$C{$^1$H} NMR (CDCl$_3$): δ 11.09, 14.05, 14.36, 21.46, 44.50, 118.11, 123.59, 125.38, 126.95, 127.95, 129.12, 129.32, 129.90, 134.55, 134.07, 137.32, 142.16, 142.00, 143.57 ppm.

EXAMPLE 41

2-(2,3,5-trimethylcyclopenta-1,4-dienyl)-4,6-dimethylphenyl(p-toluenesulfonyl)amine White solid was obtained in the same manner as in Example 40 using 0.699 g (3.075 mmol) of 2-(2,3,5-trimethylcyclopenta-1,4-dienyl)-4,6-dimethylphenylamine, 0.243 g (3.075 mmol) of pyridine, and 0.645 g (3.383 mmol) of p-toluenesulfonyl chloride (1.009 g, 86%).

$^1$H NMR (CDCl$_3$): δ 1.26(d, J=0.8 Hz, 3H, Cp—CH$_3$), 1.58 (s, 3H, Cp—CH$_3$), 1.71 (s, 3H, Cp—CH$_3$), 2.20 (s, 3H, Ph-CH$_3$), 2.31 (s, 3H, Ph-CH$_3$), 2.37 (s, 3H, Ts-CH$_3$), 2.26-2.58 (m, 2H, Cp—CH$_2$), 5.95 (s, 1H, NH$_1$), 6.54 (s, 1H, Ph), 6.93 (s, 1H, Ph), 7.03 (d, J=8.0 Hz, 2H, Ts-Ph), 7.35 (d, J=8.0 Hz, 2H, Ts-Ph) ppm.

EXAMPLE 42

2-(2,3,5-trimethylcyclopenta-1,4-dienyl)-4,6-difluorophenyl(p-toluenesulfonyl)amine White solid was obtained in the same manner as in Example 40 using 0.300 g (1.275 mmol) 2-(2,3,5-trimethylcyclopenta-1,4-dienyl)-4,6-difluorophenylamine, 0.101 g (1.275 mmol) of pyridine, and 0.267 g (1.403 mmol)$_p$-toluenesulfonyl chloride (0.340 g, 68%).

$^1$H NMR (CDCl$_3$): δ 1.53(d, J=1.2 Hz, 3H, Cp—CH$_3$), 1.78 (s, 3H, Cp—CH$_3$), 1.88 (s, 3H, Cp—CH$_3$), 2.43 (s, 3H, Ts-CH$_3$), 3.96 (qd, J=23.2, 1.6 Hz, 2H, Cp—CH$_2$), 6.26 (s, 1H, NH$_1$), 6.60-6.63 (m, 1H, Ph), 6.77-6.83 (m, 1H, Ph), 7.21 (d, J=8.4 Hz, 2H, Ts-Ph), 7.62 (d, J=8.4 Hz, 2H, Ts-Ph) ppm. $^{13}$C{$^1$H} NMR (CDCl$_3$): δ 11.66, 13.48, 14.46, 21.61, 48.78, 103.19, 112.70, 118.94, 126.74, 128.94, 133.91, 133.98, 137.40, 137.48, 138.36, 143.04, 156.58, 158.97, 161.32 ppm.

EXAMPLE 43 phenylene(p-toluenesulfonylamido)(2,3,5-trimethylcyclopentadienyl)titanium bis(dimethylamide)

0.201 g (0.569 mmol) of 2-(2,3,5-trimethylcyclopenta-1,4-dienyl)phenyl(p-toluenesulfonyl)amine and 0.128 g (0.569 mmol) of Ti(NMe$_2$)$_4$ were added to 6 mL of toluene, and then reacted at 70° C. for 12 hours. The reaction product was dried to remove all the entire volatile materials in vacuum, and then washed using 5 mL of pentane, thereby obtaining red solid.

$^1$H NMR(C$_6$D$_6$): δ 1.64(s, 3H, CH$_3$), 1.70 (s, 3H, CH$_3$), 1.83 (s, 3H, CH$_3$), 1.89 (s, 3H, CH$_3$), 3.09 (s, 6H, Ti—NMe$_2$), 3.50 (s, 6H, Ti—NMe$_2$), 5.95 (s, 1H, Cp—CH), 6.76 (d, J=7.6 Hz, 2H, Ts-Ph), 6.83 (t, J=8.0 Hz, 1H, Ph), 6.98 (d, J=8.0 Hz, 1H, Ph), 7.11 (t, J=8.0 Hz, 1H, Ph), 7.77 (d, J=7.6 Hz, 2H, Ts-Ph), 8.07 (d, J=8.0 Hz, 1H, Ph) ppm

EXAMPLE 44

4,6-dimethylphenylene(p-toluenesulfonylamido)(2,3,5-trimethylcyclopentadienyl)titanium bis(dimethylamide)

Red solid was obtained in the same manner as in Example 43 using 0.303 g (0.794 mmol) of 2-(2,3,5-trimethylcyclopenta-1,4-dienyl)-4,6-dimethylphenyl(p-toluenesulfonyl)amine and 0.179 g (0.794 mmol) of Ti(NMe$_2$)$_4$.

$^1$H NMR(C$_6$D$_6$): δ 1.88(s, 3H, CH$_3$), 1.95 (s, 3H, CH$_3$), 2.06 (s, 3H, CH$_3$), 2.14 (s, 3H, CH$_3$), 2.19 (s, 3H, CH$_3$), 3.23 (s, 6H, Ti—Me$_2$), 3.43 (s, 6H, Ti—Me$_2$), 5.93 (s, 1H, Cp—CH), 6.77 (s, 1H, Ph), 6.85 (d, J=5.6 Hz, 2H, Ts-Ph), 6.96 (s, 1H, Ph), 8.23 (d, J=5.6 Hz, 2H, Ts-Ph) ppm. $^{13}$C{$^1$H} NMR (C$_6$D$_6$): δ 11.69, 13.06, 13.44, 20.60, 21.10, 21.40, 51.89, 52.49, 113.91, 120.39, 121.87, 126.87, 127.83, 129.42, 131.49, 131.61, 132.72, 133.36, 134.33, 141.97, 142.48, 146.53 ppm

EXAMPLE 45

4,6-fluorophenylene(p-toluenesulfonylamido)(2,3,5-trimethylcyclopentadienyl)titanium bis(dimethylamide)

Red solid was obtained in the same manner as in Example 43 using 0.166 g (0.426 mmol) of 2-(2,3,5-trimethylcyclopenta-1,4-dienyl)-4,6-fluorophenyl(p-toluenesulfonyl)amine and 0.095 g (0.426 mmol) of Ti(NMe$_2$)$_4$.

$^1$H NMR(C$_6$D$_6$): δ 1.65(s, 3H, CH$_3$), 1.88 (s, 3H, CH$_3$), 1.94 (s, 3H, CH$_3$), 1.99 (s, 3H, CH$_3$), 3.07 (s, 6H, Ti—Me$_2$), 3.39 (s, 6H, Ti—Me$_2$), 5.83 (s, 1H, Cp—CH$_1$), 6.43-6.49 (m, 1H, Ph), 6.60-6.63 (m, 1H, Ph), 6.81 (d, J=8.0 Hz, 2H, Ts-Ph), 8.16 (d, J=8.4 Hz, 2H, Ts-Ph) ppm. $^{13}$C{$^1$H} NMR (C$_6$D$_6$): δ 11.26, 12.77, 13.00, 21.38, 51.82, 52.74, 104.12, 112.12, 114.39, 119.65, 120.24, 121.52, 127.01, 129.40, 131.91, 141.09, 142.35, 153.34, 155.80, 157.51, 159.93 ppm

EXAMPLE 46 phenylene(p-toluenesulfonylamido)(2,3,5-trimethylcyclopentadienyl)titanium dichloride 0.228 g (1.707 mmol) of dichlorodimethylsilane and 4 ml of toluene were added to C$_6$H$_4$(4-MePhSO$_2$N)(2,3,5-Me$_3$Cp)Ti(NMe$_2$)$_2$ that was obtained in Example 43, and then reacted at room temperature for 1 hour. The reaction product was dried to remove the volatile material in vacuum, and then washed using 3 mL of pentane, thereby obtaining yellow solid (0.228 g, 78%).

$^1$H NMR(C$_6$D$_6$): δ 1.66(br s, 3H, CH$_3$), 1.79 (s, 6H, CH$_3$), 2.26 (s, 3H, CH$_3$), 6.48 (s, 1H, Cp—CH), 6.66 (d, J=8.0 Hz, 2H, Ts-Ph), 6.86-6.88 (m, 2H, Ph), 6.99-7.02 (m, 1H, Ph), 7.11-7.13 (m, 2H, Ph), 8.16 (d, J=8.0 Hz, 2H, Ts-Ph) ppm. $^{13}$C{$^1$H} NMR (C$_6$D$_6$): δ 12.80, 15.19, 15.44, 21.41, 114.60, 124.57, 124.62, 125.63, 126.84, 128.50, 128.92, 129.27, 129.71, 130.01, 135.61, 135.69, 145.03, 155.27 ppm.

EXAMPLE 47

4,6-dimethylphenylene(p-toluenesulfonylamido)(2,3,5-trimethylcyclopentadienyl) titanium dichloride 0.307 g (2.382 mmol) of dichlorodimethylsilane and 8 mL of toluene were added to 4,6-Me$_2$C$_6$H$_4$(4-MePhSO$_2$N)(2,3,5-Me$_3$Cp)Ti(NMe$_2$)$_2$ that was obtained in Example 44, and then reacted at room temperature for one hour. The reaction product was dried in vacuum to remove the volatile material contained therein, and then washed using 9 mL of pentane, thereby obtaining yellow solid (0.327 g, 76%).

$^1$H NMR(C$_6$D$_6$): δ 1.80(s, CH$_3$), 1.84 (s, CH$_3$), 1.90 (s, CH$_3$), 1.92 (s, CH$_3$), 1.95 (s, CH$_3$), 2.11 (s, CH$_3$), 2.13 (s, CH$_3$), 2.15 (s, CH$_3$), 2.28 (s, CH$_3$), 2.29 (s, CH$_3$), 2.39 (s, CH$_3$), 6.38 (s, Cp—CH), 6.51 (s, Cp—CH), 6.61-6.64 (m, 2H, Ts-Ph), 6.64 (s, 2H, Ph), 8.08-8.12 (m, 2H, Ts-Ph) ppm.

EXAMPLE 48

4,6-fluorophenylene(p-toluenesulfonylamido)(2,3,5-trimethylcyclopentadienyl)titanium dichloride 0.165 g (1.278 mmol) of dichlorodimethylsilane and 4 ml of toluene were added to 4,6-F$_2$C6H$_4$(4-MePhSO$_2$N)(2,3,5-Me$_3$Cp)Ti(NMe$_2$)$_2$ that was obtained in Example 45, and then reacted at room temperature for one hour. The reaction product was dried in vacuum to remove the volatile material contained therein, and then washed using 4 mL of pentane, thereby obtaining yellow solid (0.166 g, 71%).

$^1$H NMR(C$_6$D$_6$): δ 1.61(s, 1.5H, CH$_3$), 1.72 (s, 1.5H, CH$_3$), 1.81 (s, 1.5H, CH$_3$), 1.82 (s, 1.5H, CH$_3$), 1.83 (s, 1.5H, CH$_3$), 1.90 (s, 1.5H, CH$_3$), 2.28 (s, 3H, CH$_3$), 6.26-6.32 (m, 2H, Ph), 6.46 (s, 0.5H, Cp—CH$_1$), 6.63 (s, 0.5H, Cp—CH$_1$), 6.70 (d, J=8.0 Hz, 2H, Ts-Ph), 8.17-8.20 (m, 2H, Ts-Ph) ppm.

EXAMPLE 49

2-(2,5-dimethylcyclopenta-1,4-dienyl)phenyl(trimethylacetyl)amine 0.130 g (1.29 mmol) of triethylamine and 0.155 g (1.29 mmol) of pivaloyl chloride were added to 0.263 g (1.42 mmol) of 2-(2,5-dimethylcyclopenta-1,4-dienyl)phenylamine solution melted in 10 mL of MC solvent, and then reacted at room temperature for 1 hour. 5 mL of 2N HCl was added to the reaction product and strongly stirred for a few minutes. The organic layer was neutralized using 5 mL of NaHCO$_3$, and the product was filtered using a column chromatography with a hexane/ethyl acetate (v/v, 10:1) solvent. The refined product was dried in vacuum to remove the solvent therein, thereby obtaining while solid (0.355 g, 93%).

$^1$H NMR (CDCl$_3$): 1.18 (s, 9H, C(CH$_3$)$_3$), 1.73 (q, J=1.6 Hz, 3H, Cp—CH$_3$), 1.89 (s, 3H, Cp—CH$_3$), 3.08-3.07 (m, 2H, Cp—CH$_2$), 6.05 (d, J=2.0 Hz, 1H, Cp—CH), 7.07 (dd, 1H, J=7.6, 2.0 Hz, 1H, bz-CH), 7.11 (td, J=7.2, 1.2 Hz, 1H, bz-CH), 7.33 (td, J=8.4, 2.0 Hz, 1H, bz-CH), 7.54 (s, 1H, NH), 8.44 (d, J=8.0 Hz, 1H, bz-CH) ppm; $^{13}$C{$^1$H} NMR (CDCl$_3$): 14.47, 14.64, 27.42, 39.84, 44.59, 119.15, 123.14, 125.27, 128.07, 129.28, 136.02, 138.36, 142.64, 142.76, 175.93 ppm.

EXAMPLE 50

2-(2,5-dimethylcyclopenta-1,4-dienyl)-3,5-dimethylphenyl(trimethylacetyl)-amine

An experiment was performed in the same manner as in Example 49 using 0.717 g (3.36 mmol) of 2-(2,5-dimethylcyclopenta-1,4-dienyl)-3,5-dimethylphenylamine, 0.408 g (4.03 mmol) of triethylamine, and 0.486 g (4.03 mmol) of pivaloyl chloride. The reaction product was filtered using a column chromatography with a toluene/MC (v/v, 1:1) solvent. The resultant reaction product was dried in vacuum to remove the solvent therein, thereby obtaining while solid (0.698 g, 70%).

$^1$H NMR (CDCl$_3$): 1.17 (s, 9H, C(CH$_3$)$_3$), 1.69 (s, 3H, Cp—CH$_3$), 1.85 (s, 3H, Cp—CH$_3$), 2.24 (s, 3H, bz-CH$_3$), 2.34 (s, 3H, bz-CH$_3$), 2.97 (d, J=1.2 Hz, 2H, Cp—CH$_2$), 5.94 (s, 1H, Cp—CH), 6.75 (s, 1H, NH), 6.78 (s, 1H, bz-CH), 7.03 (s, 1H, bz-CH) ppm; $^{13}$C{$^1$H} NMR (CDCl$_3$): 14.54, 14.58, 18.74, 21.08, 27.50, 44.19, 123.88, 127.76, 130.41, 131.19, 132.90, 134.94, 135.59, 140.14, 143.35, 175.85 ppm.

EXAMPLE 51

2-(2,5-dimethylcyclopenta-1,4-dienyl)-3,5-fluorophenyl(trimethylacetyl)-amine

Yellow solid was obtained in the same manner as in Example 49 using 0.402 g (1.82 mmol) of 2-(2,5-dimethylcyclopenta-1,4-dienyl)-3,5-fluorophenylamine, 0.202 g (2.18 mmol) of triethylamine, and 0.263 g (2.18 mmol) of pivaloyl chloride (0.347 g, 66%).

$^1$H NMR($C_6D_6$): 1.01 (s, 9H, $C(CH_3)_3$), 1.66 (s, 3H, Cp—$CH_3$), 1.72 (q, J=2.0 Hz, 3H, Cp—$CH_3$), 2.65-2.67 (m, 2H, Cp—$CH_2$), 5.79 (d, J=2.0 Hz, 1H, Cp—CH), 6.36 (s, 1H, NH), 6.52 (s, 1H, bz-CH), 6.54 (s, 1H, bz-CH) ppm; $^{13}$C{$^1$H} NMR ($C_6D_6$): 14.60, 14.63, 27.57, 39.28, 44.53, 103.58 (t, J=102.8 Hz, 1C, bz-C—F), 112.41 (dd, J=84.8, 15.2 Hz, bz-C—F), 124.60, 141.70, 142.95, 157.34 (d, J=51.6 Hz, 1C, bz-C—F), 159.62 (d, J=51.6 Hz, 1C, bz-C—F), 159.84 (d, J=54.8 Hz, 1C, bz-C—F), 162.09 (d, J=48.8 Hz, 1C, bz-C—F), 175.52 ppm.

EXAMPLE 52

2-(2,3,5-trimethylcyclopenta-1,4-dienyl)phenyl(trimethylacetyl)amine

An experiment was performed in the same manner as in Example 49 using 0.534 g (2.68 mmol) of 2-(2,3,5-trimethylcyclopenta-1,4-dienyl)phenylamine, 0.325 g (3.22 mmol) of triethylamine, and 0.388 g (3.22 mmol) of pivaloyl chloride. The reaction product was purified using a column chromatography with a hexane/ethylacetate (v/v, 5:1) solvent. The purified product was dried in vacuum to remove the solvent therein, thereby obtaining while solid (0.674 g, 89%).

$^1$H NMR ($CDCl_3$): 1.17 (s, 9H, $C(CH_3)_3$), 1.58 (s, 3H, Cp—$CH_3$), 1.83 (s, 3H, Cp—$CH_3$), 1.98 (s, 3H, Cp—$CH_3$), 3.01 (s, 2H, Cp—$CH_2$), 7.05 (dd, J=7.6, 2.0 Hz, 1H, bz-CH), 7.08 (td, 1H, J=7.6, 1.2 Hz, 1H, bz-CH), 7.30 (td, J=7.6, 1.6 Hz, 1H, bz-CH), 7.60 (s, 1H, NH), 8.44 (d, J=8.4 Hz, 1H, bz-CH) ppm; $^{13}$C{$^1$H} NMR ($CDCl_3$): 11.46, 13.51, 14.17, 27.29, 39.71, 48.87, 118.94, 122.96, 126.21, 127.78, 129.13, 134.27, 134.63, 135.91, 137.91, 137.92, 138.67, 175.75 ppm.

EXAMPLE 53

2-(2,3,5-trimethylcyclopenta-1,4-dienyl)-4,6-dimethylphenyl(trimethylacetyl)-amine The same experiment as in Example 49 was performed using 0.600 g (2.64 mmol) of 2-(2,3,5-trimethylcyclopenta-1,4-dienyl)-4,6-dimethylphenylamine, 0.321 g (3.17 mmol) of triethylamine, and 0.382 g (3.17 mmol) of pivaloyl chloride (0.727 g, 89%).

$^1$H NMR ($CDCl_3$): 1.16 (s, 9H, $C(CH_3)_3$), 1.54 (s, 3H, Cp—$CH_3$), 1.80 (s, 3H, Cp—$CH_3$), 1.94 (s, 3H, Cp—$CH_3$), 2.23 (s, 3H, bz-$CH_3$), 2.33 (s, 3H, bz-$CH_3$), 2.91 (brd, J=5.6 Hz, 2H, Cp—$CH_2$), 6.76 (s, 2H, bz-CH), 7.02 (s, 1H, NH) ppm; $^{13}$C{$^1$H} NMR ($CDCl_3$): 11.63, 13.50, 18.79, 21.09, 27.46, 39.13, 48.64, 127.68, 130.28, 131.18, 132.85, 133.22, 134.79, 135.34, 135.47, 135.62, 140.51, 175.77 ppm.

EXAMPLE 54

2-(2,3,5-trimethylcyclopenta-1,4-dienyl)-4,6-difluorophenyl(trimethylacetyl)-amine The same experiment as in Example 49 was performed using 0.463 g (1.97 mmol) of 2-(2,3,5-trimethylcyclopenta-1,4-dienyl)-4,6-fluorophenylamine, 0.239 g (2.36 mmol) of triethylamine, and 0.285 g (2.36 mmol) of pivaloyl chloride (0.400 g, 64%).

$^1$H NMR ($CDCl_3$): 1.18 (s, 9H, $C(CH_3)_3$), 1.58 (s, 3H, Cp—$CH_3$), 1.82 (s, 3H, Cp—$CH_3$), 1.94 (s, 3H, Cp—$CH_3$), 2.92 (s, 2H, Cp—$CH_2$), 6.61 (s, 1H, NH), 6.67 (dq, J=8.4, 2.8 Hz, 1H, bz-CH), 6.86 (td, 1H, J=8.4, 2.4 Hz, 1H, bz-CH) ppm; $^{13}$C{$^1$H} NMR ($CDCl_3$): 11.57, 13.48, 14.28, 27.45, 48.86, 103.26 (t, J=100.0 Hz, 1C, bz-C—F), 111.97 (dd, J=87.8, 12.4 Hz, 1C, bz-C—F), 133.71, 134.31, 137.47, 138.02, 156.19 (d, J=51.6 Hz, 1C, bz-C—F), 158.69 (d, J=51.6 Hz, 1C, bz-C—F), 158.99 (d, J=54.8 Hz, 1C, bz-C—F), 161.45 (d, J=51.6 Hz, 1C, bz-C—F), 176.00 ppm.

EXAMPLE 55 phenylene(t-butylcarboxyamido)(2,5-dimethylcyclopentadienyl)titanium bis(dimethylamide)

5 mL of toluene was added to 0.203 g (0.700 mmol) of 2-(2,5-dimethylcyclopenta-1,4-dienyl)phenyl(trimethylacetyl)amine and 0.156 g (0.700 mmol) of tetrakis(dimethylamino)titanium, and then the reaction solution was stirred at 80° C. for one day. The reaction product was dried in vacuum to remove the volatile material therein, thereby obtaining red oil. (100% purity was identified through $^1$H and $^{13}$C NMR spectroscope).

$^1$H NMR($C_6D_6$): 1.43 (s, 9H,$C(CH_3)_3$), 1.94 (s, 6H, Cp—$CH_3$), 2.97 (s, 12H, N—$CH_3$), 5.79 (s, 2H, Cp—CH), 7.01 (td, J=8.4, 1.2 Hz, bz-CH), 7.26 (t,d, J=8.4, 1.6 Hz, 1H, bz-CH), 7.30 (d, J=8.0 Hz, 1H, bz-CH), 7.66 (d, J=8.0 Hz, 1H, bz-CH) ppm; $^{13}$C{$^1$H} NMR ($C_6D_6$): 14.73 (Cp—$CH_3$), 29.14 ($C(CH_3)_3$), 39.77 ($C(CH_3)_3$), 48.35 (N—$CH_3$), 112.35, 122.81, 125.21, 125.55, 128.54, 131.55, 132.86, 144.65, 168.49 ppm.

EXAMPLE 56

4,6-dimethylphenylene(t-butylcarboxamido)(2,5-dimethylcyclopentadienyl)-titanium bis(dimethylamide)

7 mL of toluene solvent was added to 0.515 g (1.73 mmol) of 2-(2,5-dimethylcyclopenta-1,4-dienyl)-4,6-dimethylphenyl(trimethylacetyl)amine and 0.388 g (1.73 mmol) of tetrakis(dimethylamino)titanium. The reaction solution was stirred at 80° C. for 5 days, and then dried in vacuum to remove the volatile material therein, thereby obtaining red oil (almost 100% purity was identified through $^1$H and $^{13}$C NMR spectroscope).

$^1$H NMR($C_6D_6$): 1.43 (s, 9H, $C(CH_3)_3$), 1.97 (s, 6H, Cp—$CH_3$), 2.25 (s, 3H, bz-$CH_3$), 2.62 (s, 3H, bz-$CH_3$), 2.99 (s, 12H, N—$CH_3$), 5.89 (s, 2H, Cp—CH), 6.98 (s, 1H, bz-CH), 7.08 (s, 1H, bz-CH) ppm; $^{13}$C{$^1$H} NMR ($C_6D_6$): 14.95, 21.15, 21.60, 29.29, 40.30, 48.42, 112.44, 122.68, 124.72, 125.78, 130.92, 131.22, 131.38, 136.98, 140.37, 167.22 ppm.

EXAMPLE 57

4,6-difluorophenylene(t-butylcarboxamido)(2,5-dimethylcyclopentadienyl)-titanium bis(dimethylamide)

5 mL of toluene solvent was added to 0.277 g (0.87 mmol) of 2-(2,5-dimethylcyclopenta-1,4-dienyl)-4,6-difluorophenyl(trimethylacetyl)amine and 0.195 g (0.87 mmol) of tetrakis(dimethylamino)titanium. The reaction solution was stirred at 80° C. for one day, and then dried in vacuum to remove the volatile material therein, thereby obtaining red oil (almost 100% purity was identified through $^1$H and $^{13}$C NMR spectroscope).

$^1$H NMR($C_6D_6$): 1.37 (s, 9H, C($CH_3$)$_3$), 1.81 (s, 6H, Cp—$CH_3$), 2.92 (s, 12H, N—$CH_3$), 5.79 (s, 2H, Cp—CH), 6.69-6.78 (m, 2H, bz-CH) ppm; $^{13}$C{$^1$H} NMR ($C_6D_6$): 14.51, 29.04, 44.37, 48.29, 103.78 (t, J=108 Hz, 1C, bz-C—F), 112.59, 113.69 (dd, J=84.0, 15.2 Hz, 1C, bz-C—F), 123.08, 156.22 (d, J=51.6 Hz, 1C, bz-C—F), 157.52 (d, J=51.6 Hz, 1C, bz-C—F), 158.63 (d, J=51.2 Hz, 1C, bz-C—F), 160.48 (d, J=48.4 Hz, 1C, bz-C—F), 170.32 ppm.

EXAMPLE 58 phenylene(t-butylcarboxamido)(2,3,5-trimethylcyclopentadienyl)titanium bis(dimethylamide)

6 mL of toluene solvent was added to 0.486 g (1.72 mmol) of 2-(2,3,5-trimethylcyclopenta-1,4-dienyl)phenyl(trimethylacetyl)amine and 0.386 g (1.72 mmol) of tetrakis(dimethylamino)titanium. The reaction solution was stirred at 80° C. for one day, and then the volatile material therein was removed, thereby obtaining red oil (100% purity was identified through $^1$H and $^{13}$C NMR spectroscope).

$^1$H NMR($C_6D_6$): 1.45 (s, 9H, C($CH_3$)$_3$), 1.88 (s, 3H, Cp—$CH_3$), 1.94 (s, 3H, Cp—$CH_3$), 2.03 (s, 3H, Cp—$CH_3$), 2.81 (s, 6H, N—$CH_3$), 3.14 (s, 3H, N—$CH_3$), 5.86 (s, 1H, Cp—CH), 7.03 (td, J=7.2, 1.2 Hz, 1H, bz-CH), 7.27 (dd, J=7.6, 0.8 Hz, 1H, bz-CH), 7.30 (td, J=7.6, 1.2 Hz, 1H, bz-CH), 7.70 (dd, J=8.0, 0.8 Hz, 1H, bz-CH) ppm; $^{13}$C{$^1$H} NMR ($C_6D_6$): 12.79, 13.06, 14.13, 29.12, 39.76, 47.12, 49.85, 115.52, 120.22, 121.21, 121.31, 122.78, 125.59, 125.95, 128.48, 131.52, 132.95, 144.69, 168.90 ppm.

EXAMPLE 59

4,6-dimethylphenylene(t-butylcarboxamido)(2,3,5-trimethylcyclopentadienyl)titanium bis(dimethylamide)

7 mL of toluene solvent was added to 0.565 g (1.81 mmol) of 2-(2,3,5-trimethylcyclopenta-1,4-dienyl)-4,6-dimethylphenyl(trimethylacetyl)amine and 0.407 g (1.81 mmol) of tetrakis(dimethylamino)titanium. The reaction solution was stirred at 110° C. for four days, and then the volatile material therein was removed, thereby obtaining red oil (almost 100% purity was identified through $^1$H and $^{13}$C NMR spectroscope).

$^1$H NMR($C_6D_6$): 1.45 (s, 9H, C($CH_3$)$_3$), 1.92 (s, 3H, Cp—$CH_3$), 1.99 (s, 3H, Cp—$CH_3$), 2.06 (s, 3H, Cp—$CH_3$), 2.27 (s, 3H, bz-$CH_3$), 2.66 (s, 3H, bz-$CH_3$), 2.83 (s, 6H, N—$CH_3$), 3.17 (s, 6H, N—$CH_3$), 5.89 (s, 1H, Cp—CH), 6.99 (s, 1H, bz-CH), 7.10 (s, 1H, bz-CH) ppm; $^{13}$C{$^1$H} NMR ($C_6D_6$): 12.85, 13.29, 14.37, 21.19, 21.57, 29.26, 40.28, 47.22, 49.98, 115.62, 119.81, 120.77, 121.33, 125.13, 126.11, 130.89, 131.13, 131.46, 136.96, 140.39, 167.63 ppm.

EXAMPLE 60

4,6-difluorophenylene(t-butylcarboxamido)(2,3,5-trimethylcyclopentadienyl)titanium bis(dimethylamide)

5 mL of toluene solvent was added to 0.277 g (0.87 mmol) of 2-(2,3,5-trimethylcyclopenta-1,4-dienyl)-4,6-difluorophenyl(trimethylacetyl)amine and 0.195 g (0.87 mmol) of tetrakis(dimethylamino)titanium. The reaction solution was stirred at 80° C. for one day, and then the volatile material therein was removed, thereby obtaining red oil (almost 100% purity was identified through $^1$H and $^{13}$C NMR spectroscope).

$^1$H NMR($C_6D_6$): 1.41 (s, 9H, C($CH_3$)$_3$), 1.72 (s, 3H, Cp—$CH_3$), 1.84 (s, 3H, Cp—$CH_3$), 2.77 (s, 6H, N—$CH_3$), 3.09 (s, 3H, N—$CH_3$), 5.08 (s, 1H, Cp—CH), 6.73-6.79 (m, 2H, bz-CH) ppm; $^{13}$C{$^1$H} NMR ($C_6D_6$): 12.67, 12.80, 14.01, 29.04, 40.28, 47.11, 49.82, 103.67 (t, J=102.8 Hz, 1C, bz-C—F), 112.75 (dd, J=84.8, 15.2 Hz, 1C, bz-C—F), 120.08, 121.24, 121.74, 123.17, 156.24 (d, J=54.4 Hz, 1C, bz-C—F), 160.51 (d, J=51.6 Hz, 1C, bz-C—F), 170.67 ppm.

EXAMPLE 61

4,6-dimethylphenylene(t-butylcarboxamido)(2,5-dimethylcyclopentadienyl)titanium (chloride)(dimethylamide)

0.515 g (1.73 mmol) of 2-(2,5-dimethylcyclopenta-1,4-dienyl)-4,6-dimethylphenyl-(trimethylacetyl)amine and 0.388 g (1.73 mmol) of Ti(NMe$_2$)$_4$ were added to 7 mL of toluene, and then reacted at 80° C. for 5 days. The reaction product was dried in vacuum to remove the entire solvent, thereby obtaining red oil (100% purity was identified through NMR spectroscophy).

$^1$H NMR($C_6D_6$): 1.45 (s, 9H, C($CH_3$)$_3$), 1.99 (s, 6H, $CH_3$), 2.26 (s, 3H, Ph-$CH_3$), 2.66 (s, 3H, Ph-$CH_3$), 2.99 (s, 12H, N—$CH_3$), 5.88 (s, 2H, Cp-H), 7.01 (s, 1H, Ph-H), 7.10 (s, 1H, Ph-H) ppm. $^{13}$C{$^1$H} NMR ($C_6D_6$): 14.95, 21.13, 21.62, 29.27, 40.31, 48.41, 112.42, 122.68, 124.75, 125.76, 130.97, 131.25, 131.40, 137.03, 140.39, 167.26 ppm.

7 mL of toluene and 10 mL of Me$_2$SiCl$_2$ were added to the obtained bis(dimethylamido)titanium and then reacted at 80° C. for one day. The reaction product was dried in vacuum to remove the entire volatile material, and then washed using 10 mL of pentane, thereby obtaining red solid (0.340 g, 45%).

$^1$H NMR($C_6D_6$): 1.01 (s, 9H, C($CH_3$)$_3$), 1.95 (s, 3H, Ph-$CH_3$), 2.02 (s, 6H, Cp—$CH_3$), 2.18 (s, 3H, N—$CH_3$), 2.23 (s, 3H, N—$CH_3$), 2.43 (s, 3H, Ph-$CH_3$), 6.00 (d, J=2.8 Hz, 1H, Cp-H), 6.25 (d, J=2.8 Hz, 1H, Cp-H), 6.83 (s, 1H, Ph-CH), 7.44 (s, 1H, Ph-H) ppm. $^{13}$C NMR ($C_6D_6$): 17.42, 18.27, 18.93, 21.05, 30.27, 39.91, 40.82, 122.49, 123.52, 124.25, 130.03, 132.01, 137.31, 141.55, 145.65, 147.44, 163.65 ppm.

EXAMPLE 62 phenylene(t-butylcarboxamido)(2,3,5-trimethylcyclopentadienyl)titanium (chloride)(dimethylamide)

The same experiment as in Example 61 was carried out, using 2-(2,3,5-trimethylcyclopenta-1,4-dienyl)phenyl(trimethylacetyl)amine

EXAMPLE 63

4,6-difluorophenylene(t-butylcarboxamido)(2,3,5-trimethylcyclopentadienyl)titanium (chloride)(dimethylamide)

The same experiment as in Example 61 was carried out, using 2-(2,3,5-trimethylcyclopenta-1,4-dienyl)-4,6-difluorophenyl(trimethylacetyl)amine.

EXAMPLE 64

4,6-difluorophenylene(t-butyliminooxy)(2,5-dimethylcyclopentadienyl)-titanium dichloride 0.271 g (2.10 mmol) of dichlorodimethylsilane and 5 mL of toluene were added to 4,6-F$_2$C6H$_2$(t-BuCON)(2,5-Me$_2$Cp)Ti(NMe$_2$)$_2$. The reaction solution was stirred at room temperature for 1 hour. The reaction product was dried in vacuum to remove the volatile material therein, washed using 10 mL of pentane solvent, and then dried in vacuum to remove the solvent, thereby obtaining yellow solid. (0.177 g, 60%). The crystalline structure of the product is illustrated in FIG. 2.

$^1$H NMR(C$_6$D$_6$): 1.33 (s, 9H,C(CH$_3$)$_3$), 1.81 (s, 6H, Cp—CH$_3$), 6.08 (s, 2H, Cp—CH), 6.15 (dq, J=9.2, 3.2 Hz, 1H, bz-CH), 6.54 (tdq, J=8.4, 3.6, 3.2 Hz, 1H, bz-CH) ppm; $^{13}$C{$^1$H} NMR (C$_6$D$_6$): 16.42, 28.64, 42.10, 103.20 (t, J=103.2 Hz, 1C, bz-C—F), 113.85 (dd, J=92.0, 15.2 Hz, 1C, bz-C—F), 122.46, 132.43, 157.69 (d, J=51.6 Hz, 1C, bz-C—F), 158.59 (d, J=51.6 Hz, 1C, bz-C—F), 160.15 (d, J=54.8 Hz, 1C, bz-C—F), 161.09 (d, J=51.6 Hz, 1C, bz-C—F), 168.29 ppm.

EXAMPLE 65

(4,6-difluoro)phenylene(t-butyliminooxy)(2,3,5-trimethylcyclopentadienyl)-titanium dichloride 0.377 g (2.61 mmol) of dichlorodimethylsilane and 5 mL of toluene were added to 4,6-F$_2$C6H$_2$(t-BuCON)(2,3,5-Me$_3$Cp)Ti(NMe$_2$)$_2$. The reaction solution was stirred at room temperature for 8 hours. The reaction product was dried in vacuum to remove the volatile material, washed using 10 mL of pentane solvent and then dried in vacuum to remove the solvent, thereby obtaining yellow solid (0.378 g, 89%).

$^1$H NMR(C$_6$D$_6$): 1.34 (s, 9H, C(CH$_3$)$_3$), 1.74 (s, 3H, Cp—CH$_3$), 1.89 (s, 3H, Cp—CH$_3$), 2.03 (s, 3H, Cp—CH$_3$), 5.91 (s, 1H, Cp—CH), 6.24 (dt, J=9.2, 2.4 Hz, 1H, bz-CH), 6.57 (tdt, J=8.4, 3.6, 2.0 Hz, 1H, bz-CH) ppm; $^{13}$C{$^1$H} NMR (C$_6$D$_6$): 14.12, 15.58, 16.69, 28.66, 42.04, 105.39 (t, J=103.2 Hz, 1C, bz-C—F), 113.76 (dd, J=92.0, 18.0 Hz, 1C, bz-C—F), 123.83, 130.68, 131.35, 135.90, 157.67 (d, J=51.6 Hz, 1C, bz-C—F), 158.67 (d, J=51.6 Hz, 1C, bz-C—F), 160.12 (d, J=54.8 Hz, 1C, bz-C—F), 161.17 (d, J=51.6 Hz, 1C, bz-C—F), 168.69, 175.45 ppm.

EXAMPLE 66 phenylene(t-butylcarboxamido)(2,5-dimethylcyclopentadienyl)dilithium salt 1.31 g (4.86 mmol) of 2-(2,5-dimethylcyclopenta-1,4-dienyl)phenyl(trimethylacetyl)amine was melted in 25 mL of diethyl ether. Then, 2.70 g of nBuLi (2.5 M in hexane) was slowly added thereto at −30° C. and stirred at room temperature for 6 hours. The reaction product was filtered using 10 mL of diethyl ether, and the used solvent was removed, thereby obtaining yellow salt in which the number of coordinated diethyl ethers was 0.39. (1.33 g, 89%).

$^1$H NMR(C$_5$D$_5$N): δ 1.35 (s, 9H, C(CH$_3$)$_3$), 2.26 (s, 6H, CH$_3$), 6.28 (s, 2H, Cp-H), 6.90 (td, J=6.8, 1.6 Hz, 1H, H$^{4\ or\ 5}$), 7.01 (td, J=7.2, 1.6 Hz, 1H, H$^{4\ or\ 5}$), 7.76 (dd, J=7.6, 2.4 Hz, 1H, H$^{3\ or\ 6}$), 7.89 (d, J=8.0 Hz, 1H, H$^{3\ or\ 6}$) ppm. $^{13}$C{$^1$H} NMR (C$_5$D$_5$N): δ 15.57, 29.86, 39.81, 103.50, 113.58, 115.13, 119.70, 123.99, 126.33, 131.13, 137.79, 153.18, 178.54 ppm.

EXAMPLE 67 phenylene(t-butylcarboxamido)(2,3,5-trimethylcyclopentadienyl)dilithium salt An experiment in the same as Example 66 was carried out, using 1.28 g (4.52 mmol) of 2-(2,3,5-trimethylcyclopenta-1,4-dienyl)phenyl-(trimethylacetyl)amine. As a result, a yellow salt in which the number of coordinated diethyl ethers was 0.29. (1.40 g, 92%).

$^1$H NMR(C$_5$D$_5$N): δ 1.35 (s, 9H, C(CH$_3$)$_3$), 2.12 (s, 3H, CH$_3$), 2.28 (s, 3H, CH$_3$), 2.45 (s, 3H, CH$_3$), 6.11 (s, 1H, Cp-H), 6.90 (t, J=6.8 Hz, 1H, H$^{4\ or\ 5}$), 7.02 (t, J=7.2 Hz, 1H, H$^{4\ or\ 5}$), 7.76 (d, J=7.6 Hz, 1H, H$^{3\ or\ 6}$), 7.89 (d, J=7.6 Hz, 1H, H$^{3\ or\ 6}$) ppm. $^{13}$C{$^1$H} NMR (C$_5$D$_5$N): δ 12.90, 14.73, 15.38, 29.86, 39.77, 104.54, 110.31, 110.73, 111.16, 114.19, 119.61, 123.79, 126.32, 131.23, 138.08, 153.28, 178.48 ppm.

EXAMPLE 68 phenylene(t-butylcarboxamido)(2,5-dimethylcyclopentadienyl)titanium dimethyl 0.361 g (1.29 mmol) of TiCl$_4$DME was melted in 16 mL of diethyl ether. Then, 1.61 mL of MeLi (1.6 M in diethyl ether) was added thereto at 0° C. and stirred for 15 minutes. Next, 0.400 g (1.29 mmol) of <C6H$_2$(t-BuCON)(2,5-Me$_2$Cp)>Li$_2$ was added to the reaction product and stirred for 3 hours. The solvent contained in the resultant reaction product was removed, and then the product was filtered using 15 mL of pentane. The used pentane was removed thereby obtaining dark green solid. (0.320 g, 72%). The crystalline structure of the product is illustrated in FIG. 3.

$^1$H NMR(C$_6$D$_6$): δ 1.12 (s, 6H, T$_1$-CH$_3$), 1.36 (s, 9H, C(CH$_3$)$_3$), 1.62 (s, 6H, Cp—CH$_3$), 6.46 (s, 2H, Cp-H), 6.85 (td, J=7.2, 1.2 Hz, 1H, H$^{4\ or\ 5}$), 6.98 (td, J=7.2, 1.2 Hz, 1H, H$^{4\ or\ 5}$), 7.01-7.04 (m, 2H, H$^{3\ and\ 6}$) ppm.

EXAMPLE 69 phenylene(t-butylcarboxamido)(2,3,5-trimethylcyclopentadienyl)titanium dimethyl An experiment was performed in the same manner as in Example 68 using 0.331 g (1.18 mmol) of TiCl$_4$-DME, 1.48 ml of MeLi (1.6M in diethyl ether), and 0.400 g (1.18 mmol) of <C6H$_2$(t-BUCON)(2,3,5-Me$_3$Cp)>Li$_2$ (0.320 g, 75%).

$^1$H NMR(C$_6$D$_6$): δ 0.95 (s, 3H, T$_1$-CH$_3$), 1.23 (s, 3H, T$_1$-CH$_3$), 1.36 (s, 9H, C(CH$_3$)$_3$), 1.51 (s, 3H, Cp—CH$_3$), 1.66 (s, 3H, Cp—CH$_3$), 2.16 (s, 3H, Cp—CH$_3$), 6.25 (s, 1H, Cp-H), 6.87 (t, J=7.2 Hz, 1H, H$^{4\ or\ 5}$), 6.99 (t, J=8.4 Hz, 1H, H$^{4\ or\ 5}$), 7.03 (d, J=8.0 Hz, 1H, H$^{3\ or\ 6}$), 7.07 (d, J=8.0 Hz, 1H, H$^{3\ or\ 6}$) ppm.

COMPARATIVE EXAMPLE 1 butylidene(2,5-dimethylcyclopentadienyl)(cyclopentadienyl)titanium dichloride 26.52 g (95.68 mmol.) of normal butyl lithium was added to 10.4 g (47.84 mmol) of 2-(1-cyclopenta-1,4-dienyl-butyl)-1,3-dimethyl-cyclopenta-1,3-diene melted in 60 mL of a cold tetrahydrofuran in a nitrogen atmosphere via schlenkline. Then, the reaction solution was stirred for 12 hours, dried in a reduced pressure to remove a third of the solvent, filtered, and then washed using hexane, thereby obtaining lithium salt compound with an yield of 95%. The obtained lithium salt (3.38 g) was melted in pyridine to decrease the temperature thereof to −30° C. Separatly, 1.5 g (8.7 mmol) of Ti(NMe$_2$)$_2$Cl$_2$ was melted in toluene and then the temperature of the resultant solution was decreased to the same temperature. Then, the prepared two solutions were quickly mixed and reacted for 20 minutes. The reaction product was dried to remove the solvent and filtered using pentane, thereby obtaining a titan compound that is substituted with a dimethyl amino group.

$^1$H NMR (pyridine-d$_5$): δ 6.33 (s, 1H, Cp-H), 6.32 (s, 1H, Cp-H), 6.14 (d, J=2.8 Hz, 1H, Me$_2$Cp-H), 6.08 (d, J=2.8 Hz, 1H, Me$_2$Cp-H), 5.22 (s, 1H, Cp-H), 5.03 (s, 1H, Cp-H), 3.61 (t, 1H, CHCH$_2$), 2.99 (d, J=8.4 Hz 12H, NCH$_3$), 1.95 (s, 3H, CH$_3$), 1.82 (s, 3H, CH$_3$), 1.47 (quartet, J=7.2H, 3H, CHCH$_3$) ppm.

The titan compound that is substituted with a dimethyl amino group was melted in 35 mL of pentane, and then 2 eq. of Me$_2$SiC2 (2.11 mL) was added thereto. The reaction solution was reacted for 30 minutes. Then, the red color of the product disappeared and a solid was formed. Only the solid was collected, melted with benzene, and then left sat for 12 hours. The generated solid was filtered and the used solvent was removed, thereby obtaining a titan-containing bridged metallocene compound (Yield: 50%).

$^1$H NMR(C$_6$D$_6$): δ 6.77 (quartet, J=2.4 Hz, 1H, Cp-H$^{3\ or\ 4}$), 6.68 (m, 1H, Cp-H$^{3\ or\ 4}$), 6.67 (d, J=4 Hz, 1H, Me$_2$Cp-H), 6.64 (d, J=4 Hz, 1H, Me$_2$Cp-H), 5.19 (dd, J=3.2, 2.8 Hz, 1H, Cp-H$^{1\ or\ 5}$), 5.02 (dd, J=3.2, 2.8 Hz, 1H, Cp-H$^{1\ or\ 5}$), 3.62 (t, 1H, bridge), 1.74 (s, 3H, CH$_3$), 1.59 (s, 3H, CH$_3$) ppm.

COMPARATIVE EXAMPLE 2 bis(n-butylcyclopentadienyl)zirconium dichloride

The zirconium metal compound was purchased from US Boulder Scientific Co. and directly used for ethylene copolymerization.

COMPARATIVE EXAMPLE 3 iso-propylidene(cyclopentadienyl)(9-fluorenyl)zirconium dichloride

The zirconium metal compound was purchased from US Boulder Scientific Co. and directly used for ethylene homopolymerization.

Ethylene Homopolymerization

EXAMPLE 70

Ethylene Homopolymerization in the Presence of 1,2-C$_6$H$_4$(2,4,6-Me$_3$PhSO$_2$N)(2,5-Me$_2$Cp)TiCl$_2$ 250 mL of toluene solvent was loaded to a 500 mL glass reactor. Then, 1.0 mol of the titanium compound that was treated with 25 mol of triisobutylaluminum compound, and 5.0 mol of trityl tetrakis(pentafluorophenyl)borate cocatalyst were sequentially added thereto. Right after the reactor was shaken in an oil bath at 90° C. for 2 minutes at a rate of 300 rpm, ethylene pressure (40 psig) was added to the reactor to perform polymerization at 90° C. for 5 minutes. The residual ethylene gas was removed. Then, excess ethanol was added to the reaction product to induce the polymer precipitation. The obtained polymer was washed with ethanol and acetone two to three times, respectively. The washed product was dried in an oven at 80° C. for 12 hours or more. The mass of the measured polymer was 3.26 g, and the degree of activity of the catalyst was 39.1 Kg PE/mmol-Ti hr.

EXAMPLE 71

Ethylene Homopolymerization in the Presence of 1,2-C$_6$H$_4$(4-MePhSO$_2$N)(2,5-Me$_2$Cp)TiCl$_2$ Ethylene homopolymerization was performed in the same manner as in Example 70 using 1.0 mol of the titanium compound. The mass of the measured polymer was 1.10 g, and the degree of activity of the catalyst was 13.2 Kg PE/mmol-Ti hr.

EXAMPLE 72

Ethylene Homopolymerization in the Presence of 1,2-C$_6$H$_4$(MeSO$_2$N)(2,5-Me$_2$Cp)TiCl$_2$ Ethylene homopolymerization was performed in the same manner as in Example 70 using 1.0 mol of the titanium compound. The mass of the measured polymer was 0.33 g, and the degree of activity of the catalyst was 4.0 Kg PE/mmol-Ti hr.

COMPARATIVE EXAMPLE 5

Ethylene Homopolymerization in the Presence of H$_3$C(CH$_2$)$_3$CH(2,5-Me$_2$Cp)(Cp)TiCl$_2$ Ethylene homopolymerization was performed for 10 minutes in the same manner as in Example 70 using 2.5 mol of the titanium compound. The mass of the measured polymer was 2.25 g, and the degree of activity of the catalyst was 5.40 Kg PE/mmol-Ti hr.

Ethylene Copolymerization

EXAMPLE 73

Copolymerization of Low-Pressure Ethylene and 1-octene 250 mL of toluene solvent and a proper amount of 1-octene were added to a 500 mL glass reactor. Then, a 1.0 micromole of a titanium compound that was treated with 25 micromole of triisobutylaluminum compound, and 5.0 micromole of trityl tetrakis(pentafluorophenyl)borate cocatalyst were sequentially added thereto. The reactor was placed in an oil bath at 90° C., and then 40 psig of ethylene pressure was added to the reactor to perform polymerization for 10 minutes. The residual ethylene gas was removed, and then excess ethanol was added to the reaction product to induce the polymer precipitation. The obtained polymer was washed with ethanol and acetone two to three times, respectively, and then dried at 80° C. for 12 hours or more.

EXAMPLE 74

Copolymerization of High-Pressure Ethylene and 1-octene 1.0 L of toluene solvent and a proper amount of 1-octene were added to a 2 L autoclave reactor. Then, the reactor was preheated at 90° C. and at the same time, the reactor was filled with 6 bar of ethylene. 5.0 micromole of titanium compound that was treated with 125 micromole of triisobutylaluminum compound, and 25 micromole of trityl tetrakis(pentafluorophenyl)borate cocatalyst were sequentially added to a 25 mL catalyst storage tank. At this time, 13 bar of ethylene was added to the catalyst storage tank to perform copolymerization for 10 minutes. The residual ethylene gas was removed, and then excess ethanol was added to the polymer solution to induce precipitation. The obtained polymer was washed with ethanol and acetone two to three times, respectively, and then dried at 80° C. for 12 hours or more.

EXAMPLE 75

Copolymerization of High-Pressure Ethylene and 1-octene 1.0 L of toluene solvent and 1-octene (fixed at 0.8 M) were added to a 2 L autoclave reactor. Then, ethylene copolymerization was carried out in the same manner as in Example 74 using various titanium compounds (5.0 micromole).

EXAMPLE 76

Copolymerization of high-pressure ethylene and 1-octene 1.0 L of hexane solvent and 1-octene (fixed at 0.8 M) were added to a 2 L autoclave reactor. Then, ethylene copolymerization was carried out in the same manner as in Example 74 using various titanium compounds (5.0 micromole) at 140° C. at an ethylene pressure of 35 bar.

Properties Measurement (Weight, Activity, Melt Index, Melting Point, and Density A melt index (MI) of a polymer was measured using ASTM D-1238 (Condition E, 190° C., 2.16 Kg weight). A melting point ($T_m$) of the polymer was a Differential Scanning Calorimeter (DSC) 2920 produced by TA Co. That is, the DSC curve of the polymer was obtained by increasing the temperature to 200° C., maintaining at 200° C. for 5, decreasing to 30° C., and then increasing. The summit of the DSC curve corresponds to a melting point. At this time, the increase and decrease rates of the temperature were 10° C./min, and the melting point was obtained in a second temperature increase period.

In order to measure the density of the polymer, a sample that had been treated with 1,000 ppm of an antioxidant was formed into a sheet having a thickness of 3 mm and a diameter of 2 cm by a 180° C. press mold, and then the prepared sheet was cooled to 10° C./min. The cooled sheet was measured using a mettler scale.

EXPERIMENTAL EXAMPLE 1

Copolymerization of Ethylene and 1-octene

Various properties of copolymers prepared according to Example 73 using transition metal complexes prepared according to Examples 32, 35, and 39 and Comparative Example 1. The results are shown in Table 1.

TABLE 1

| Complex used | 1-octene (M) | Polymer Weight (g) | Activity (Kg/mmol-Ti hr) | Melt Index[a] (g/10 min) | Melting Point (° C.) | Branch Amount (mol %) |
|---|---|---|---|---|---|---|
| Example 32 | 0.1 | 2.3 | 13.8 | 19.5 | 89.5 | 89.5 |
| Example 35 | 0.1 | 4.7 | 28.3 | Not measurable | 96.7 | 11 |
| Example 35 | 0.3 | 2.0 | 12.0 | Not measurable | Not measurable | 25 |
| Example 39 | 0.1 | 0.57 | 3.2 | Has not been measured | | |
| Comparative Example 1[b] | 0.1 | 1.09 | 6.54 | Has not been measured | | |

[a] $I_2$ value,
[b] the weight average molecular weight (Mw) of a polymer obtained using a compex of Comparative Example 1 was 108,150

As shown in Table 1, a degree of copolymerization activity of the catalyst complexes synthesized in Examples 32, 35, and 39 is dependent on a substitutent of nitrogen. For example, the complex that was synthesized according to Example 35 in which p-toluenesulfonyl was introduced to nitrogen, showed high activity compared to other catalysts complexes having the same concentration of octane. Almost all of the complexes having a phenylene bridge according to the present invention showed high copolymerization activity, and high reactivity to an olefin monomer having a large steric hindrance, such as 1-octene, compared to when the complex having biscyclopentadienyl of Comparative Example 1 was used.

EXPERIMENTAL EXAMPLE 2

Copolymerization of Ethylene and 1-octene

Properties of copolymers prepared according to Example 74 using the transition metal complexes synthesized according to Examples 32, 35, and 39 were measured. The results are shown in Table 2.

TABLE 2

| Complex used | 1-octene (M) | Activity (g/10 min) | Melt Index[a] (g/10 min) | Melting Point (° C.) | Density (g/cc) |
|---|---|---|---|---|---|
| Example 32 | 0.3 | 34.4 | 6.8 | 108.9 | 0.915 |
| Example 32 | 0.5 | 23.0 | 16.6 | 98.7 | 0.900 |
| Example 32 | 0.8 | 16.8 | Not measurable | Not measurable | Not measurable |

TABLE 2-continued

| Complex used | 1-octene (M) | Activity (g/10 min) | Melt Index[a] (g/10 min) | Melting Point (° C.) | Density (g/cc) |
|---|---|---|---|---|---|
| Example 35 | 0.1 | 55.1 | 3.02 | 121.7 | 0.934 |
| Example 35 | 0.1[b] | 40.8 | 1.35 | 122.3 | 0.935 |
| Example 35 | 0.3 | 50.8 | 3.70 | 107.7 | 0.912 |
| Example 35 | 0.5 | 78.4 | 43 | 103.0 | 0.899 |
| Example 35 | 0.8 | 87.2 | 103 | 89.8 | 0.883 |
| Example 35 | 1.2 | 82.3 | Not measurable | Not measurable | 0.865 |
| Example 39 | 0.1 | 24.7 | 60.8[c] | 121.1 | 0.931 |
| Example 39 | 0.3 | 24.2 | 4.1 | 110.0 | 0.915 |
| Comparative Example 1 | 0.3 | 85.2 | 2.57 | 121.0 | has not been measured |

[a]$I_2$ value,
[b]reaction temperature of 110° C.,
[c]$I_{21}$ value

As shown in Table 2, the complex prepared according to Example 35 showed higher copolymerization activity than other complexes, and an increase of the activity continued to some level as the concentration of octene increased. Almost all of the complexes showed low activity compared to the complex of Comparative Example 1, but a copolymer that was synthesized using the complexes to which a bridge is introduced according to the present invention had lower density than when the complex having a bisphenylenecyclopentadienyl group of Comparative Example 1 was used, which indicates high reactivity of the complex according to the present invention with respect to an olefin monomer having a large steric hindrance, such as 1-octene.

EXPERIMENTAL EXAMPLE 3

Copolymerization of Ethylene and 1-octene

Properties of copolymers prepared according to Example 74 using the transition metal complexes synthesized according to Examples 35, 46-48, 61-64, and 69 and Comparative Examples 2 and 3 were measured. The results are shown in Table 3.

TABLE 3

| Complex used | Polymer Mass (g) | Activity (Kg/mmol-Ti hr) | Melt Index[a] (g/10 min) | Melting Point (° C.) | Density (g/cc) |
|---|---|---|---|---|---|
| Example 46 | 80.04 | 96.05 | 26 | 92.8 | 0.877 |
| Example 47 | 3.39 | 4.07 | 2.70 | Not measurable | 0.891 |
| Example 48 | 5.06 | 6.07 | 0.23 | 90.7 | 0.858 |
| Example 61 | 7.06 | 8.47 | 0.14 | 112.9 | 0.879 |
| Example 62 | 34.96 | 41.95 | 0.33 | 74.8 | 0.870 |
| Example 63 | 44.01 | 52.81 | 3.85 | Not measurable | 0.852 |
| Example 64 | 17.03 | 20.44 | 0.26 | 62.0 | 0.861 |
| Example 69 | 55.70 | 66.84 | 0.64 | 63.4 | 0.872 |
| Comparative Example 2 | 118.8 | 142.5 | 100 | 120.7 | 0.939 |
| Comparative Example 3 | 112.1 | 134.6 | 66.4 | 98.5 | 0.910 |

[a]$I_2$ value

As shown in Table 3, the complexes in which t-butylcarbonyl(butylcarbonyl) was introduced to nitrogen prepared according to Examples 61 through 64, and 69 showed lower copolymerization activity than the complexes in which a sulfonyl group is introduced to a nitrogen prepared according to Example 46. However, a polymer synthesized using the complexes in which t-butylcarbonyl(butylcarbonyl) was introduced to nitrogen prepared according to Examples 61 through 64, and 69 had high molecular weight. The catalyst complexes according to the present invention showed lower activity than the catalyst complexes of Comparative Example 2 and 3, but a copolymer that was synthesized using the catalyst complexes according to the present invention had higher molecular weight and higher polymer density of 0.860 g/cc. Thus, the catalyst complexes according to the present invention showed excellent copolymerization reactivity.

EXPERIMENTAL EXAMPLE 4

Copolymerization of Ethylene and 1-octene

Properties of copolymers prepared according to Example 76 using the transition metal complexes synthesized according to Examples 46 and 69. The results are shown in Table 4.

TABLE 4

| Complex used | Polymer Mass (g) | Activity (Kg/mmol-Ti hr) | Melt Index[a] (g/10 min) | Melting Point (° C.) | Density (g/cc) |
|---|---|---|---|---|---|
| Example 46 | 21.33 | 12.80 | | Has not been measured | |
| Example 69 | 28.89[b] | 11.56 | | Has not been measured | |

[a]$I_2$ value,
[b]polymerization for 15 minutes

[a]$I_2$ value, [b] polymerization for 15 minutes

As shown in Table 4, as a result of copolymerization at high temperature and high pressure, it was found that the catalyst complexes according to the present invention was stably used for copolymerization at high temperature of 140° C.

Compared to a conventional transition metal complex having a silicon bridge and an oxido ligand, a transition metal complex according to the present invention has a phenylene bridge, so that a monomer easily approaches the transition metal complex in terms of structure and a pentagon ring structure of the transition metal complex is stably maintained. By using a catalyst composition including the transition metal complex, a polyolefin copolymer having a very low density less than 0.910 g/cc can be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A transition metal complex of Formula 1:

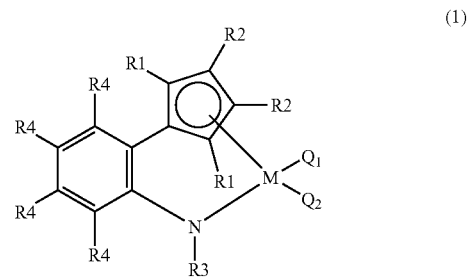

(1)

where R1 and R2 are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein R1 and R2 can be connected by an alkylidene radical that contains a C1-C20 alkyl or aryl radical to form a ring;

R4 is each independently a hydrogen atom; a halogen radical; or a C1-C20 alkyl or aryl radical, wherein two R4 can be connected to form a fused ring structure;

R3 is a C1-C20 alkyl sulfonyl, aryl sulfonyl, or silyl sulfonyl radical; a C1-C20 alkyl carbonyl, aryl carbonyl, or silyl carbonyl radical; C1-C20 alkyl carboxy, or aryl carboxy radical; or C1-C20 alkyl phosphonyl, or aryl phosphonyl radical;

M is a transition metal of Group 4; and

Q1 and Q2 are each independently a halogen radical; a C1-C20 alkyl or aryl amido radical; a C1-C20 alkyl, alkenyl, aryl, alkylaryl, or arylalkyl radical; or a C2-C20 alkylidene radical.

2. The transition metal complex of claim 1, being represented by Formula 14:

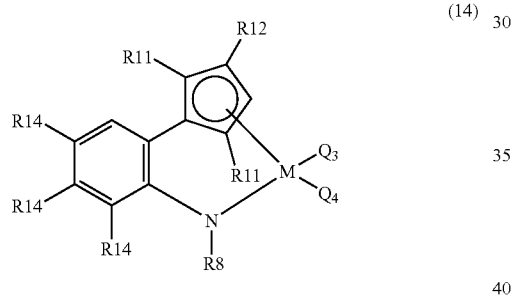

(14)

where R1 and R12 are each independently hydrogen atom; or C1-C20 alkyl, aryl, or silyl radical;

R14 is each independently hydrogen atom; a C1-C20 alkyl radical; or halogen radical;

Q3 and Q4 are each independently a halogen radical; C1-C20 alkyl, or aryl amido radical; or C1-C20 alkyl radical;

M is a transition metal of Group 4; and

R8 is

where Y is a carbon atom or a sulfur atom;

R9 is a hydrogen atom; a C1-C20 alkyl, aryl, or silyl radical; or a C1-C20 alkoxy, or aryloxy radical; and when Y is the carbon atom, n is 1, and when Y is the sulfur atom, n is 2.

3. The transition metal complex of claim 1, being represented by one of the formulae below:

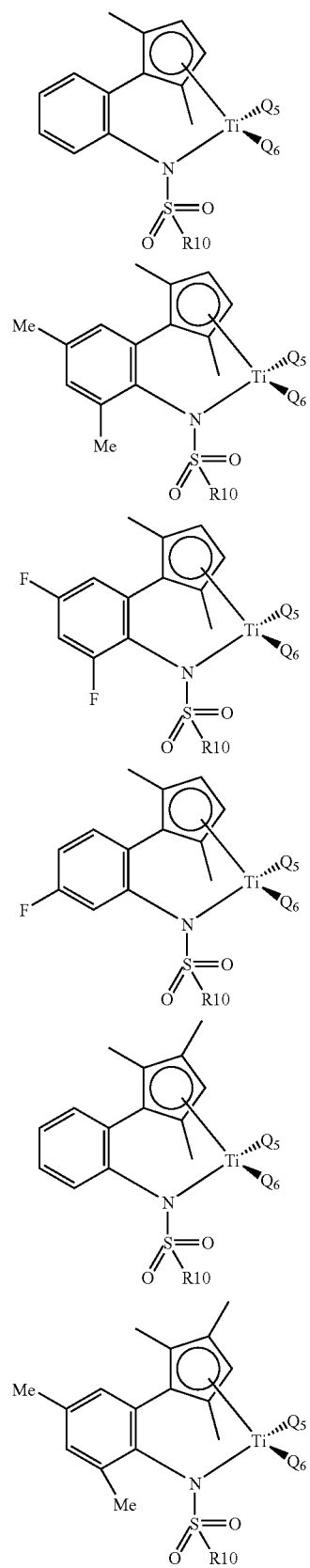

-continued

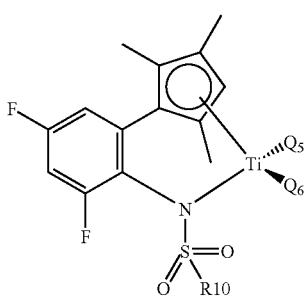
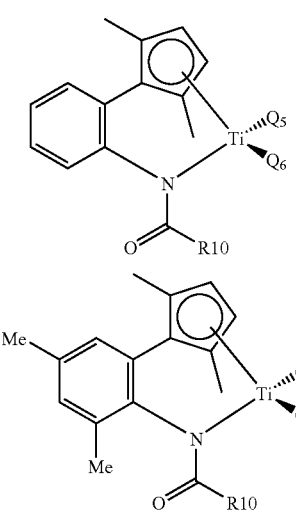
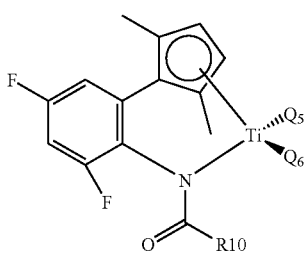
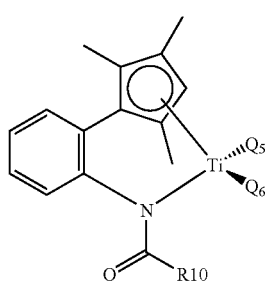
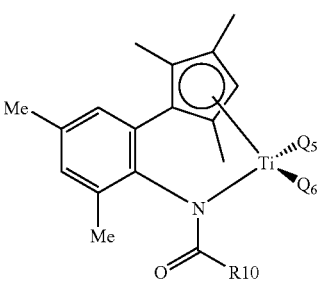

-continued

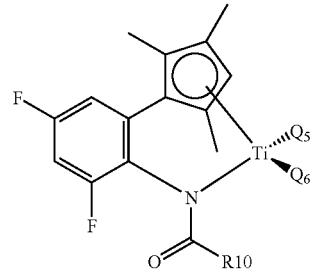

where R10 is a methyl radical, a tosyl radical, a mesityl radical, or a t-butyl radical; Q5 and Q6 are each independently a methyl radical, a dimethylamido radical, or a chloride radical.

4. A transition metal complex of Formula 2:

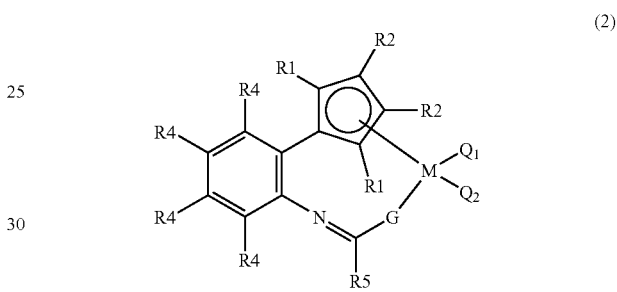

(2)

where R1 and R2 are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein R1 and R2 can be connected by an alkylidene radical that contains a C1-C20 alkyl or aryl radical to form a ring;

R4 is each independently a hydrogen atom; a halogen radical; or a C1-C20 alkyl or aryl radical, wherein two R4 are connected to form a fused ring structure;

M is a transition metal of Group 4;

Q1 and Q2 are each independently a halogen radical; a C1-C20 alkyl or aryl amido radical; a C1-C20 alkyl, alkenyl, aryl, alkylaryl, or arylalkyl radical; or a C2-C20 alkylidene radical;

G is an oxygen atom or a sulfur atom; and

R5 is a hydrogen atom; a C1-C20 alkyl or aryl radical; or a C1-C20 aryloxy radical.

5. The transition metal complex of claim 4, being represented by one of the formulae below:

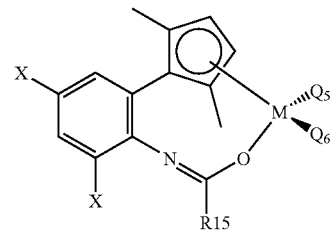

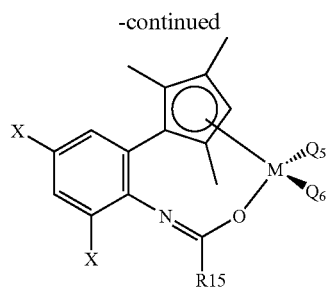

where R15 is a methyl radical, a t-butyl radical, or a t-butoxy radical; Q5 and Q6 are each independently a methyl radical, a dimethylamido radical, or a chloride radical; and X is a halogen radical.

6. A transition metal complex of Formula 3:

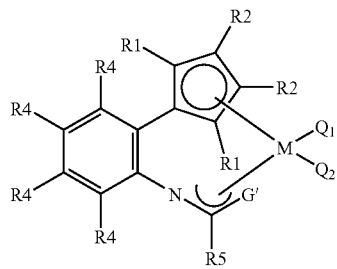

(3)

where R1 and R2 are each independently a hydrogen atom; a C1-C20 alkyl, aryl, or silyl radical; a C1-C20 alkenyl, alkylaryl, or arylalkyl radical; or a metalloid radical of Group 14 metal substituted with hydrocarbyl, wherein R1 and R2 can be connected by an alkylidene radical that contains a C1-C20 alkyl or aryl radical to form a ring;

R4 is each independently a hydrogen atom; a halogen radical; or a C1-C20 alkyl or aryl radical, wherein two R4 can be connected to form a fused ring structure;

R5 is a hydrogen atom; a C1-C20 alkyl or aryl radical; or a C1-C20 alkoxy or aryloxy radical;

M is a transition metal of Group 4;

Q1 and Q2 are each independently a halogen radical; a C1-C20 alkyl or aryl amido radical; a C1-C20 alkyl, alkenyl, aryl, alkylaryl, or arylalkyl radical; or a C2-C20 alkylidene radical; and G' is an oxygen atom or a sulfur atom.

7. The transition metal complex of claim 6, being represented by one of the formulae below:

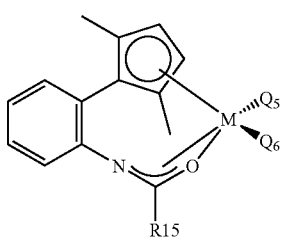

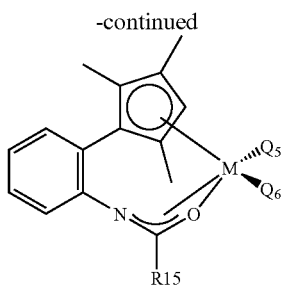

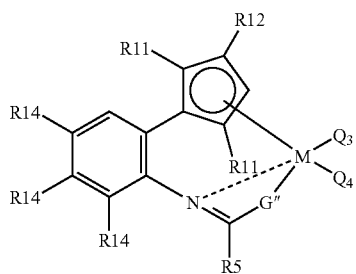

where R15 is a methyl radical, a t-butyl radical, or a t-butoxy radical; Q5 and Q6 are each independently a methyl radical, a dimethylamido radical, or a chloride radical; and X is a halogen radical.

8. A transition metal complex of Formula 16:

(16)

where R1 and R12 are each independently hydrogen atom; or C1-C20 alkyl, aryl, or silyl radical;

R14 is each independently a hydrogen atom; a C1-C20 alkyl radical; or a halogen radical;

Q3 and Q4 are each independently a halogen radical; a C1-C20 alkyl or aryl amido radical; or a C1-C20 alkyl radical R5 is a hydrogen atom; a C1-C20 alkyl or aryl radical; or a C1-C20 alkoxy or aryloxy radical; M is a transition metal of Group 4;
and G" is an oxygen atom or a sulfur atom.

* * * * *